US007993289B2

(12) United States Patent
Quistgaard et al.

(10) Patent No.: US 7,993,289 B2
(45) Date of Patent: *Aug. 9, 2011

(54) SYSTEMS AND METHODS FOR THE DESTRUCTION OF ADIPOSE TISSUE

(75) Inventors: Jens U. Quistgaard, Seattle, WA (US); Tim Etchells, Bothell, WA (US); Gregory Paul Darlington, Snohomoish, WA (US); Charles S. Desilets, Edmonds, WA (US)

(73) Assignee: Medicis Technologies Corporation, Bothell, WA (US)

( * ) Notice: Subject to any disclaimer, the term of this patent is extended or adjusted under 35 U.S.C. 154(b) by 1193 days.

This patent is subject to a terminal disclaimer.

(21) Appl. No.: 11/026,519

(22) Filed: Dec. 29, 2004

(65) Prior Publication Data
US 2005/0154431 A1 Jul. 14, 2005

Related U.S. Application Data

(63) Continuation-in-part of application No. 10/750,370, filed on Dec. 30, 2003, now abandoned, and a continuation-in-part of application No. 10/751,344, filed on Dec. 30, 2003, now abandoned.

(60) Provisional application No. 60/533,988, filed on Dec. 30, 2003, provisional application No. 60/533,958, filed on Dec. 30, 2003.

(51) Int. Cl.
*A61N 7/00* (2006.01)
(52) U.S. Cl. .............................. 601/2; 601/3
(58) Field of Classification Search .................. 600/439, 600/444; 601/2–4; 604/22
See application file for complete search history.

(56) References Cited

U.S. PATENT DOCUMENTS

| 3,880,393 | A | | 4/1975 | Watson |
| 4,002,221 | A | | 1/1977 | Buchalter |
| 4,059,098 | A | | 11/1977 | Murdock |
| 4,137,777 | A | | 2/1979 | Haverl et al. |
| 4,196,630 | A | * | 4/1980 | Rudolph .................. 73/633 |
| 4,211,949 | A | | 7/1980 | Brisken et al. |
| 4,291,578 | A | * | 9/1981 | Hetz et al. .................. 73/633 |

(Continued)

FOREIGN PATENT DOCUMENTS

GB 820814 9/1959

(Continued)

OTHER PUBLICATIONS

Ayme et al., "Occurance of Transient Cavitation in Pulsed Swatooth Ultrasonic Fields", *J. Acoust. Soc. Am.* (1988) 84(5):1598-1605.

(Continued)

*Primary Examiner* — Ruth S Smith
*Assistant Examiner* — Christopher Cook
(74) *Attorney, Agent, or Firm* — Kilpatrick Townsend & Stockton LLP

(57) ABSTRACT

Described is a system and method for the destruction of adipose tissue using an energy applicator such as a HIFU transducer. The system has a scan head containing an energy applicator, a mechanical arm for carrying the weight of the scan head, and a therapy controller such as a computer for controlling the operation of the scan head. The therapy controller may be part of a general purpose computer, and may be used as a robotic controller to automate the procedure. Methods are included for destroying adipose tissue in a quick, non-invasive manner.

6 Claims, 12 Drawing Sheets

U.S. PATENT DOCUMENTS

| Patent Number | | Date | Inventor(s) | Ref |
|---|---|---|---|---|
| 4,326,418 | A | 4/1982 | Pell, Jr. | |
| 4,368,410 | A * | 1/1983 | Hance et al. | 318/116 |
| 4,421,118 | A * | 12/1983 | Dow et al. | 600/446 |
| 4,437,033 | A | 3/1984 | Diepers | |
| 4,444,197 | A * | 4/1984 | Koyano et al. | 600/443 |
| 4,459,854 | A | 7/1984 | Richardson et al. | |
| 4,501,557 | A | 2/1985 | Tamura et al. | |
| 4,530,358 | A | 7/1985 | Forssmann et al. | |
| 4,543,959 | A * | 10/1985 | Sepponen | 600/440 |
| 4,552,151 | A | 11/1985 | Bolomey et al. | |
| 4,556,066 | A | 12/1985 | Semrow | |
| 4,567,895 | A | 2/1986 | Putzke | |
| 4,593,699 | A | 6/1986 | Poncy et al. | |
| 4,854,808 | A | 8/1989 | Bruno | |
| 4,865,042 | A | 9/1989 | Umemura et al. | |
| 4,901,073 | A | 2/1990 | Kibrick | |
| 4,932,414 | A * | 6/1990 | Coleman et al. | 600/445 |
| 4,938,217 | A * | 7/1990 | Lele | 601/3 |
| 4,955,365 | A | 9/1990 | Fry et al. | |
| 4,960,107 | A | 10/1990 | Aida et al. | |
| 5,064,340 | A | 11/1991 | Genov et al. | |
| 5,078,144 | A | 1/1992 | Sekino et al. | |
| 5,102,380 | A | 4/1992 | Jacobson et al. | |
| 5,143,063 | A * | 9/1992 | Fellner | 601/3 |
| 5,195,509 | A | 3/1993 | Rentschler et al. | |
| 5,219,401 | A | 6/1993 | Cathignol et al. | |
| 5,259,383 | A | 11/1993 | Holstein et al. | |
| 5,301,660 | A | 4/1994 | Rattner | |
| 5,308,222 | A | 5/1994 | Bacchi et al. | |
| 5,352,301 | A | 10/1994 | Panchanathan et al. | |
| 5,382,286 | A | 1/1995 | Fanning et al. | |
| 5,404,387 | A | 4/1995 | Hammond et al. | |
| 5,419,327 | A | 5/1995 | Rohwedder et al. | |
| 5,419,761 | A | 5/1995 | Narayanan et al. | |
| 5,434,208 | A | 7/1995 | Batelaan et al. | |
| 5,476,438 | A | 12/1995 | Edrich et al. | |
| 5,477,736 | A | 12/1995 | Lorraine | |
| 5,505,206 | A | 4/1996 | Walloch | |
| 5,526,815 | A | 6/1996 | Granz et al. | |
| 5,568,810 | A | 10/1996 | Hamers et al. | |
| 5,613,419 | A | 3/1997 | Pierson et al. | |
| 5,618,275 | A | 4/1997 | Bock | |
| 5,623,928 | A | 4/1997 | Wright et al. | |
| 5,626,554 | A | 5/1997 | Ryaby et al. | |
| 5,669,150 | A | 9/1997 | Guertin et al. | |
| 5,676,159 | A | 10/1997 | Navis | |
| 5,695,500 | A | 12/1997 | Taylor et al. | |
| 5,722,411 | A | 3/1998 | Suzuki et al. | |
| 5,738,098 | A | 4/1998 | Brock-Fisher et al. | |
| 5,738,635 | A | 4/1998 | Chapelon et al. | |
| 5,755,753 | A | 5/1998 | Knowlton | |
| 5,762,066 | A * | 6/1998 | Law et al. | 600/439 |
| 5,769,790 | A | 6/1998 | Watkins et al. | |
| 5,797,849 | A * | 8/1998 | Vesely et al. | 600/461 |
| 5,816,269 | A | 10/1998 | Mohammed | |
| 5,820,623 | A * | 10/1998 | Ng | 606/1 |
| 5,827,204 | A | 10/1998 | Grandia et al. | |
| 5,852,413 | A | 12/1998 | Bacchi et al. | |
| 5,871,446 | A * | 2/1999 | Wilk | 600/407 |
| 5,928,169 | A | 7/1999 | Schatzle et al. | |
| 5,938,608 | A | 8/1999 | Bieger et al. | |
| 5,938,922 | A | 8/1999 | Fulk, Jr. et al. | |
| 6,039,048 | A | 3/2000 | Silberg | |
| 6,039,689 | A | 3/2000 | Lizzi | |
| 6,039,694 | A | 3/2000 | Larson et al. | |
| 6,071,239 | A | 6/2000 | Cribbs et al. | |
| 6,085,749 | A * | 7/2000 | Wardle et al. | 128/845 |
| 6,113,558 | A | 9/2000 | Rosenschein et al. | |
| 6,126,619 | A | 10/2000 | Peterson et al. | |
| 6,142,748 | A | 11/2000 | Harris et al. | |
| 6,152,137 | A | 11/2000 | Schwartz et al. | |
| 6,217,515 | B1 | 4/2001 | Yamakawa et al. | |
| 6,233,476 | B1 | 5/2001 | Strommer et al. | |
| 6,241,753 | B1 | 6/2001 | Knowlton | |
| 6,261,249 | B1 | 7/2001 | Talish et al. | |
| 6,264,605 | B1 | 7/2001 | Scirica et al. | |
| 6,302,848 | B1 | 10/2001 | Larson et al. | |
| 6,306,146 | B1 | 10/2001 | Dinkler | |
| 6,309,355 | B1 | 10/2001 | Cain et al. | |
| 6,312,211 | B2 | 11/2001 | Tranchida | |
| 6,321,106 | B1 * | 11/2001 | Lemelson | 600/407 |
| 6,350,245 | B1 | 2/2002 | Cimino | |
| 6,366,831 | B1 * | 4/2002 | Raab | 700/262 |
| 6,368,331 | B1 | 4/2002 | Front et al. | |
| 6,419,648 | B1 | 7/2002 | Vitek et al. | |
| 6,423,077 | B2 * | 7/2002 | Carol et al. | 606/130 |
| 6,425,867 | B1 * | 7/2002 | Vaezy et al. | 600/439 |
| 6,488,639 | B1 | 12/2002 | Ribault et al. | |
| 6,506,171 | B1 | 1/2003 | Vitek et al. | |
| 6,507,309 | B2 | 1/2003 | McMakin et al. | |
| 6,524,250 | B1 * | 2/2003 | Weber et al. | 600/439 |
| 6,554,826 | B1 | 4/2003 | Deardorff | |
| 6,561,389 | B1 | 5/2003 | Earle | |
| 6,575,906 | B1 | 6/2003 | Schembri, Jr. et al. | |
| 6,595,934 | B1 | 7/2003 | Hissong et al. | |
| 6,607,498 | B2 | 8/2003 | Eshel | |
| 6,613,004 | B1 | 9/2003 | Vitek et al. | |
| 6,618,620 | B1 | 9/2003 | Freundlich et al. | |
| 6,644,852 | B2 * | 11/2003 | Crain et al. | 378/197 |
| 6,685,639 | B1 | 2/2004 | Wang et al. | |
| 6,773,408 | B1 * | 8/2004 | Acker et al. | 601/2 |
| 6,829,990 | B2 | 12/2004 | Cochran et al. | |
| 6,936,046 | B2 | 8/2005 | Hissong et al. | |
| 7,695,437 | B2 * | 4/2010 | Quistgaard et al. | 600/446 |
| 2001/0031922 | A1 * | 10/2001 | Weng et al. | 600/439 |
| 2002/0128592 | A1 | 9/2002 | Eshel | |
| 2003/0083536 | A1 * | 5/2003 | Eshel et al. | 600/2 |
| 2003/0083572 | A1 * | 5/2003 | Satragno et al. | 600/411 |
| 2003/0171701 | A1 | 9/2003 | Babaev | |
| 2003/0187431 | A1 | 10/2003 | Simonson | |
| 2004/0039312 | A1 | 2/2004 | Hillstead et al. | |
| 2004/0215110 | A1 | 10/2004 | Kreindel | |
| 2005/0015024 | A1 | 1/2005 | Babaev | |
| 2005/0043726 | A1 | 2/2005 | McHale et al. | |
| 2005/0055018 | A1 | 3/2005 | Kreindel | |
| 2005/0154314 | A1 | 7/2005 | Quistgaard et al. | |
| 2005/0187495 | A1 | 8/2005 | Quistgaard et al. | |
| 2005/0203490 | A1 | 9/2005 | Simonson | |
| 2005/0228319 | A1 | 10/2005 | Kenny | |
| 2006/0122509 | A1 | 6/2006 | Desilets | |
| 2006/0211958 | A1 | 9/2006 | Rosenberg et al. | |

FOREIGN PATENT DOCUMENTS

| | | |
|---|---|---|
| JP | 06-233776 A | 8/1994 |
| JP | 08-024267 A | 1/1996 |
| JP | 2000-210300 A | 8/2000 |
| JP | 2002-516586 T | 6/2002 |
| WO | WO 98/58588 A1 | 12/1998 |
| WO | WO 00/36982 | 6/2000 |
| WO | WO 02/054018 | 7/2002 |

OTHER PUBLICATIONS

Clarke et al., "Physical and Chemical Aspects of Ultrasonic Disruption of Cells," *J. Acoust. Soc. Am.* (1970) 47(2):649-653.

Flynn et al., "A Mechanism for the Generation of Cavitation Maxima by Pulsed Ultrasound," *J. Acoust. Soc. Am.* (1984) 76(2):505-512.

Fry et al., "Threshold Ultrasonic Dosages for Structural Changes in the Mammalian Brain," *J. Acoust. Soc. Am.* (1970) 48(6):1413-1417.

Kinney, "Body Contouring with External Ultrasound," *Plastic & Reconstruct. Surg.* (1999) 103:728-729.

Padmaker, "Thresholds and Mechanisms of Ultrasonic Damage to 'organized' Animal Tissues *Symposium on Biological Effects and Characterizations of Ultrasound Sources*,"(1977) Hazzard et al., Eds., pp. 224-239.

Romer Cimcore, "Infinite" [brochure], retrieved from the Internet: < http://www.romer.com/main/index.php> on Nov. 11, 2005, 1 page only.

Office Action of Japanese Patent Application No. 2006-547563, mailed Jun. 3, 2010, 4 pages total (English Translation Included).

Supplementary European Search Report of patent application No. 04815910.7, mailed Dec. 6, 2010, 5 pages total.

* cited by examiner

SYSTEMS AND METHODS FOR THE DESTRUCTION OF ADIPOSE TISSUE

CROSS-REFERENCES TO RELATED APPLICATIONS

This application is a continuation-in-part of application Ser. No. 10/750,370, filed on Dec. 30, 2003 now abandoned, and a continuation-in-part of application Ser. No. 10/751,344, filed on Dec. 30, 2003 now abandoned.

This application also claims the benefit of prior provisional application No. 60/533,988, filed on Dec. 30, 2003, and of prior provisional application No. 60/533,958, filed on Dec. 30, 2003. The full disclosures of each of the above applications is incorporated herein by reference.

The subject matter of the present application is related to that of the following applications: Ser. No. 10/750,369, filed on Dec. 30, 2003, now abandoned, entitled "Disposable Transducer Seal"; 60/533,528, entitled "Position Tracking Device"; 60/534,036, entitled "Ultrasound Therapy Head with Movement Control"; and 60/534,034, entitled "Component Ultrasound Transducer"; the full disclosure of each of these applications are incorporated herein by reference.

BACKGROUND OF THE INVENTION

1. Field of the Invention

The present invention relates to systems and methods for the destruction of adipose tissue (fat).

2. Description of the Prior Art

Body sculpting has developed into a highly sought after procedure for reducing a person's weight and restoring people to a leaner, trimmer physique. The field of cosmetic surgery has ballooned considerably with developments in both tools and techniques. One popular procedure for both quick weight loss and body sculpting is liposuction.

Liposuction is a method of body contouring that can dramatically improve the shape and contour of different body areas by sculpting and removing unwanted fat. More than 200,000 liposuction procedures are performed annually. Recent innovations and advances in the field of liposuction include the tumescent technique and an ultrasonic assisted technique. Traditional liposuction was done by making small incisions in desired locations, then inserting a hollow tube or cannula under the skin in the fat layer. The cannula is connected to a vacuum and the fat is vacuumed out under high suction pressure. This procedure indiscriminately removed fat, connective tissue, blood vessels and nerve tissue. The procedure caused bleeding, bruising, trauma, and blood loss, restricting the amount of fat removal possible.

The Tumescent technique allows for removal of significantly more fat during the operation with less blood loss. Tumescent liposuction injects a fat layer with large amounts of saline and adrenalin solution before suctioning. A cannula is again used with a suction device to remove fat. This procedure reduces the bleeding of traditional liposuction. However the procedure still removes a significant amount of structural tissue, blood and nerve endings.

The most recently approved innovation is Ultrasound Assisted Lipoplasty (UAL). UAL utilizes a titanium cannula that has the tip vibrating at ultrasound frequency. This vibration disrupts the near volume fat cells and essentially liquefies them for easy removal. UAL uses a low power suction and draws the fat material only in the near vicinity of the cannula tip. This technique is more refined and gentle to the tissues, there is less blood loss, less bruising, less pain, and a significantly faster recovery.

The use of ultrasound for surgical procedure is not restricted to UAL. High intensity focused ultrasound (HIFU) techniques have been employed by others for cancer therapy.

U.S. Pat. No. 6,309,355 to Cain et al., discloses a method of generating micro-bubbles in a target tissue and then using an ultrasound source to cause the micro bubbles to create a cavitation effect to destroy nearby tissue. The preferred embodiment utilizes a low frequency ultrasound source (less than 500 kHz) to cause the cavitation. A diagnostic instrument is used to determine the location of the individual surgical lesions.

PCT application WO 02/054018 A2 to Eshel, et al., provides for a method of lysing adipose tissue in a region of the human body while simultaneously not lysing non-adipose tissue. The method describes the use of HIFU in the body coupled to a diagnostic imaging system and a computer to track the areas being irradiated with HIFU energy.

There have been several innovations in the development of HIFU over the past decade. Intensities have been increased to a point where boiling occurs in a very short period of time (~1 second) as bubbles are formed from cavitation. Bubbles greatly increase the absorption of ultrasound and concomitant rapid heating of tissue. The Haifu (Chongqing, China) company has produced a therapy device for the treatment of solid tumors using ultrasound. Ultrasound energy is applied while an applicator is moving within a water bag surrounding a tumor containing tissue.

Other treatment regimens rely primarily on thermal mechanisms to necrose tissue. Several papers report creating cavitation in tissue without necessarily increasing tissue temperatures to necrotic levels. These methods apply high intensity continuous wave (CW) ultrasound regimens to tissue in order to create cavitation bubbles (sometimes referred to as "stable" cavitation), the primary purpose of these bubbles is to enhance absorption and decrease heating times. Applying therapy with very high intensity short pulses which are rapidly repeated similar to pulse wave (PW) ultrasound can create cavitation bubbles with generally very short lifetimes (micro seconds). These bubbles cause significant mechanical damage to tissue that can be periodically repeated by short (~5-30 second) pulses without a lot concomitant tissue heating. Soliciting regimen parameters carefully can enhance mechanical damage through shear forces, transient cavitation shock waves, or stable cavitation pressures for example without necessarily heating tissue to thermal necrosis levels.

HIFU therapy can be applied several ways and combination of ways. Most HIFU regimens have been applied by locating the HIFU application at one spot and turning on the power for a given period of time, typically 1 to 4 seconds. Intensity levels are typically chosen so as to heat tissue at the focal point of the applicator to the point of coagulative necrosis, although others report heating the tissue past the boiling point of water (100 C). After a period of insonification, the applicator is turned off and moved to a new location; typically a few mm away from the previous application. The applicator is not turned on again until the tissue has had a period of time to cool, which can be anywhere from a few seconds to a few minutes. The applicator is turned on again and a new lesion is created. Treating a large volume of tissue can take hours with such an approach.

The following additional references are relevant in the art: U.S. Pat. Nos. 5,769,790; 6,113,558; 5,827,204; 5,143,063; 5,219,401; 5,419,761; 5,618,275; 6,039,048; 6,425,867; 5,928,169; 6,387,380; 6,350,245; 6,241,753; 5,526,815; 6,071,239; 5,143,063; 6,685,639 and WO 00/36982.

The above mentioned references discuss ultrasound technology relevant to the present invention, and methods of using them to destroy tissue within a person's body. However there is a noticeable short coming among the prior art. There is no teaching for allowing a patient and a physician to work together to plan a desired body sculpting plan to achieve a result the patient will find desirable. There is no means in the prior art for storing information accurately from one treatment session to the next as to what has been done in a patient. This necessitates that all treatment be done at one time, which creates the possibility a patient will be over treated, or the physician must guess by either feeling or looking at a patient's adipose tissue regions to determine what has been done in a previous session. Where a patient has undergone a non-invasive HIFU treatment, the physician will be completely lost and unable to determine what appropriate follow on treatment is desired.

Furthermore the ultra sound procedures of the prior art suffer from the ability to treat large volumes of tissue quickly. Thus as far as treating volume or mass quantities, invasive procedures are preferred.

Therefore it is an object of the present invention to provide for a means through which a patient and physician can determine an appropriate therapy treatment and get a sense for the results achievable.

It is further an object of the present invention to provide a means for the accurate determination of a the volume of adipose tissue in a patient.

Still another objective of the present invention is to provide a means for the precise tracking of therapy procedures and their effects in a patient so a patient may spread the course of a desired therapy out over time to reduce or eliminate the discomfort and danger of doing a large scale procedure all at one time.

It is further an objective of the present invention to provide a means for the accurate mapping of surgical legion placement within a human body.

It is still further an objective of the present invention to provide for means and methods for the rapid destruction of adipose tissue in volumes similar to those of invasive procedures.

Any one or more of these objects are addressed in the following disclosure.

BRIEF SUMMARY OF THE INVENTION

Described herein are systems and methods for the destruction of adipose tissue. In a first embodiment there is a system for the application of energy to a body region, the system comprising a scan head including an energy applicator, a means for suspending the scan head in space and a therapy controller coupled to the scan head and the suspending means. The therapy controller is adapted to monitor the position and energy delivery of the scan head while providing guidance for positioning the scan head.

In a second embodiment there is a system for producing a matched topographical and near surface subcutaneous tissue map, the system comprises a three dimensional imaging apparatus for producing surface images of a patient body; a tissue imaging apparatus for producing subcutaneous images of the patient body; and a correlative operation device for matching a plurality of markers of the surface image and the subcutaneous image.

In a third embodiment there is a system for positioning a medical device, the system comprises; a robotic arm; a first control means for controlling the robotic arm; a medical device movably positioned within a therapy head, the therapy head being connected to the robotic arm; a second control means for controlling the movement of the medical device within the therapy head; and an electronic controller in electronic communication with, and for the cooperative operation of, the robotic arm, the first control means, the medical device and the second control means.

In still another embodiment, there is a system for positioning a medical device, the system comprising; a robotic arm; a control means for controlling the robotic arm; a medical device fixedly positioned within a therapy head, the therapy head being connected to the robotic arm; and an electronic controller for translating movement instructions received from the control means, and relaying the movement instructions to the robotic arm.

In another embodiment, there is an apparatus for guiding the movement of an energy emitter over a patient body, the apparatus comprising; a movable therapy head having at least one energy emitter; a guide ring; and a tracking system for following the movement of the guide ring and keeping the therapy head substantially centered within the guide ring.

In yet another embodiment there is a system for positioning a medical device, the system comprising: a load balancing arm; a medical device movably positioned within a therapy head, the therapy head being connected to the load balancing arm; and a means for controlling the movement of the medical device within the therapy head.

There are also methods for using the systems described. In one embodiment there is a method for applying energy to a body region, the method comprising the steps of first, providing a treatment plan to a treatment controller, second manually scanning a scan head over a body surface in response to guidance generated by the treatment controller while energy is being delivered from said scan head, third monitoring the position of and energy delivery from the scan head to produce position data and transferring the position data to the treatment controller; and last, generating an alert if the manual position and/or the energy delivery fall outside of the treatment plan.

In a second embodiment there is a method of performing a lipoplasty procedure comprising the steps of: (a) determining the suitability of a person for therapeutic ultrasound treatment; (b) marking areas to be treated on the person; (c) positioning the patient for a therapeutic ultrasound procedure; (d) scanning the marked areas into a computer; (e) setting the therapeutic ultrasound procedure using a procedure planning software package; (f) activating the therapeutic ultrasound procedure using a computer system controlled through the procedure planning software; (g) recording the progress of the therapy procedure using the procedure planning software; and (h) providing the person with any additional post operative assistance as may be dictated.

In another embodiment, there is a method of destroying adipose tissue in a patient using therapeutic ultrasound comprising the steps of determining one or more locations of adipose tissue on the patient, positioning the patient on to a treatment bed, and irradiating the locations of adipose tissue of the patient with a therapeutic ultrasound transducer.

In yet another embodiment, a method of creating a 3D body map is disclosed. The method of creating a 3D body map with the locations of adipose tissue volumes comprising the steps of generating a 3D image of the body using a 3D imaging system, entering the 3D image of the body into a computer readable format, creating a 3D body map of the body with a 3D mapping software application, and scanning the body with a diagnostic ultrasound device in electronic communication with the 3D mapping software application such that the regions of adipose tissue detected by the diagnostic ultrasound device are properly placed in the 3D body map.

In still another embodiment there is a method of body sculpting utilizing a 3D body map comprising the steps of analyzing a 3D body map for volumes of adipose tissue to be destroyed, determining the amount of adipose tissue that may be safety destroyed using a body sculpting procedure, subtracting the volume of adipose tissue to be destroyed to produce a second 3D body map, wherein a physician and a patient may compare the first 3D body map and any plurality of second 3D body maps to select the desired amount of body sculpting procedure to be preformed.

In another embodiment there is a method for destroying adipose tissue comprising the steps of; determining a volume and area of tissue to be treated; and treating the volume with a pulse wave (PW) HIFU transducer swept over the area in a continuous motion.

In still another embodiment, there is a method for positioning an ultrasound therapy head in space using a load balancing arm, the therapy head comprising a movement controller for an energy applicator suspended within the therapy head. The method comprising the steps of: first applying a force to the therapy head and second, providing electronic guidance to the movement controller.

DETAILED DESCRIPTION OF THE INVENTION

Definitions

In the present discussion we refer to a "therapy controller" as a device responsible for the planning, coordination and operation of the medical procedures used with the present invention. The therapy controller is a computer device. It may be a dedicated, specially constructed computer system or a general purpose computer with sufficient hardware and software resources to provide command and control of the present system: Namely the control of the therapy head, energy emitter and mechanical arm to the extent necessary. We some times refer to treatment planning software, a treatment controller, or a program for performing ultrasound therapy. Each of these elements refers in general to the roll of the therapy controller as a functional element of the present invention or a particular sub unit of the therapy controller.

Furthermore, we use the term "electronic communication" herein to include all forms of electronic signal and power compling between components, whether hardware or software. Thus we refer to the sending of data, instruction, code, and/or power as electronic communication, whether such sending is one way, two way, or in response to a query or instruction or demand for such electrical power or information. Any intentional movement of electrons between parts is "electronic communication."

By "therapy head" we mean a housing for containing the energy applicator. The housing may be specially designed to be form fitted over the energy applicator minimizing the bulk of the housing, or a housing having additional volume for the incorporation of additional devices. Such devices may include a small motor system for moving the energy applicator within the housing, or the use of a fluid reservoir, or having additional sensors, guidance devices for relaying information to components positioned to the exterior of the therapy head. In previous descriptions we assign the term "end effector" or "effector" to the "therapy head." The use of the terms "therapy head", "effector", "scan head" and "end effector" are considered interchangeable.

HIFU System Description

The present invention is a system for the application of energy to a body region. The system has three principle subsystems: a scan head, a suspension device and a treatment controller. The scan head includes an energy applicator and a fluid reservoir. The suspension device is typically a mechanical arm. The third component is a therapy controller in electronic communication with the scan head and the means for suspending the scan head. The therapy controller is adapted to monitor the position and/or energy delivery of the scan head while providing guidance for positioning the scan head.

Figure 1:
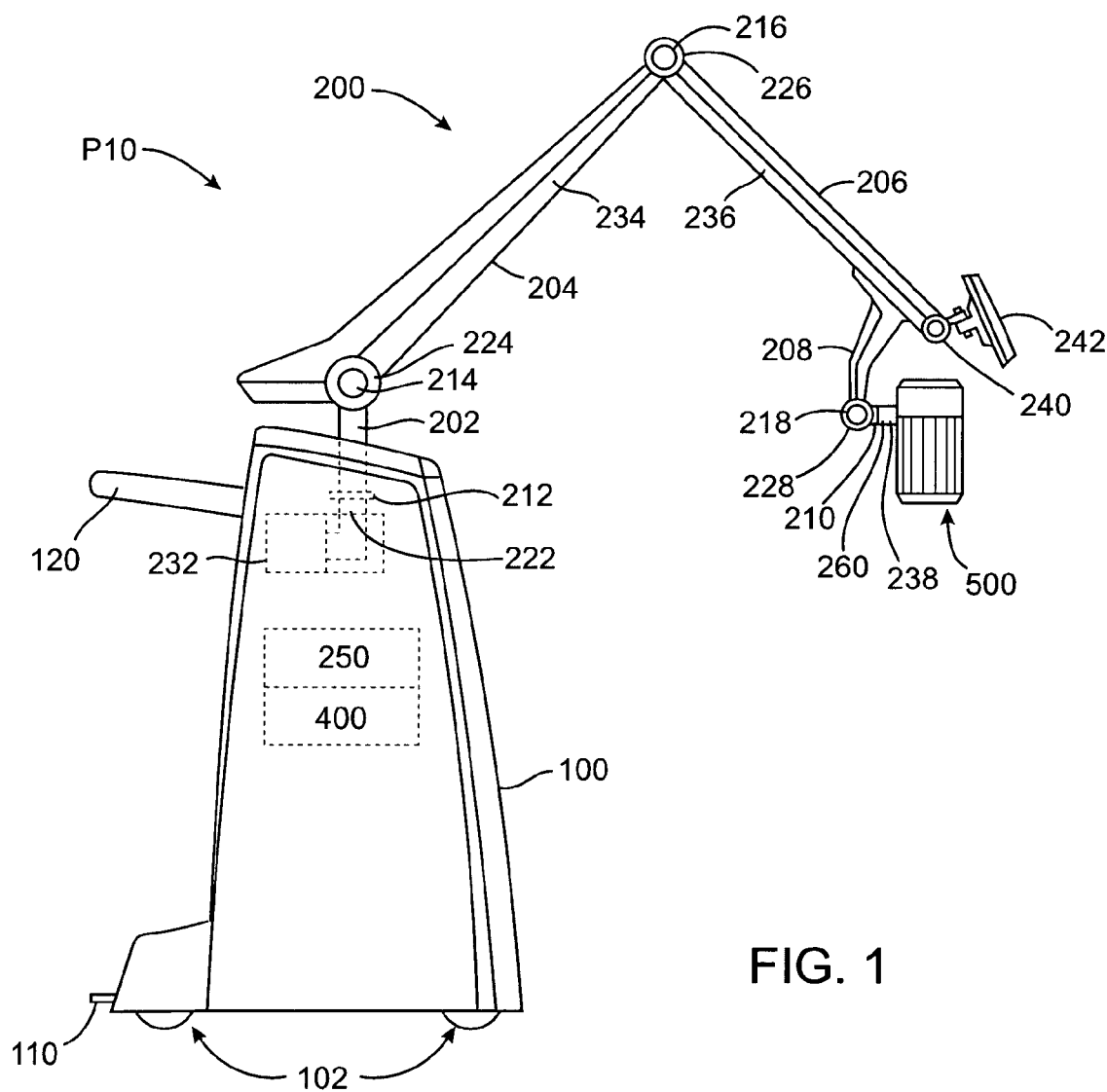
FIG. 1 illustrates a side view of the present invention.

The system P10 of the present invention has a scan head 500 that includes an energy applicator 600 (see FIG. 1). The system P10 also has a means for suspending the scan head in space, such as a mechanical arm 200. The suspending means carries the majority of the weight of the scan head 500 and permits either a user to manually reposition the scan head 500 in space, or for the scan head to be moved robotically through a robotic controller. The suspending means may also providing tracking information relevant to the location of the scan head relative to a patient's body. Data may be gathered from the scan head 500 as it is moving through space to provide tracking information of the scan head. There is also a therapy controller 250 coupled to the scan head and the suspending means. The therapy controller may be part of a computer 400 or a separate intelligent device. The therapy controller monitors the position and energy delivery of the scan head while providing guidance to a user on where to move the scan head relative to the patient's body.

The system 10 has a base 100, optionally mounted on a plurality of castors 102. A wheel brake 110 may be used to secure the base 100 in place. An optional handle 120 may be used to move the base 100. The base 100 contains a therapy controller 250 as an independent device, or as part of a larger computer 400. Optional motive generating devices, such as a motor 232 may also be contained in the base 100. The mechanical arm 200 is anchored to the base 100 through a stem 202. A rotational joint 212 may also contain a rotational encoder 222.

Each arm segment has a corresponding joint 214, 216, 218 and optional encoder 224, 226, 228. The arm segments 204, 206, 208 extend from the base and support the therapy head (or scan head) 500. A retainer 260 is used to connect the therapy head 500 to the distal most segment 208 of the mechanical arm 200. Additional joints 240, 210 provide added degrees of freedom to the therapy head 500 or an optional display device 242. Contained within each arm segment are force generating devices 234, 236, 238 used to move the therapy head 500 in space, or to counter balance the weight of the therapy head.

We now discuss each of the subsystems in turn.

Scan Head

The scan head (also called the therapy head) is a housing containing an energy applicator, and any additional devices needed for the effective operation of the energy applicator during a therapeutic procedure. Multiple designs may be selected from for use in the scan head sub system. The therapy head is generally configured as an inverted cup or bell, having a chamber with an aperture at the bottom of the therapy head.

The chamber may be divided into two sections, forming an upper chamber and a lower chamber, with a seal between them. The upper chamber contains such electronic and motor drive units such as are needed for the manipulation and control of the energy applicator. The lower chamber contains the energy applicator, ultrasound coupling fluid and such sensors as are deemed necessary for the proper operation of the system.

Figure 2:
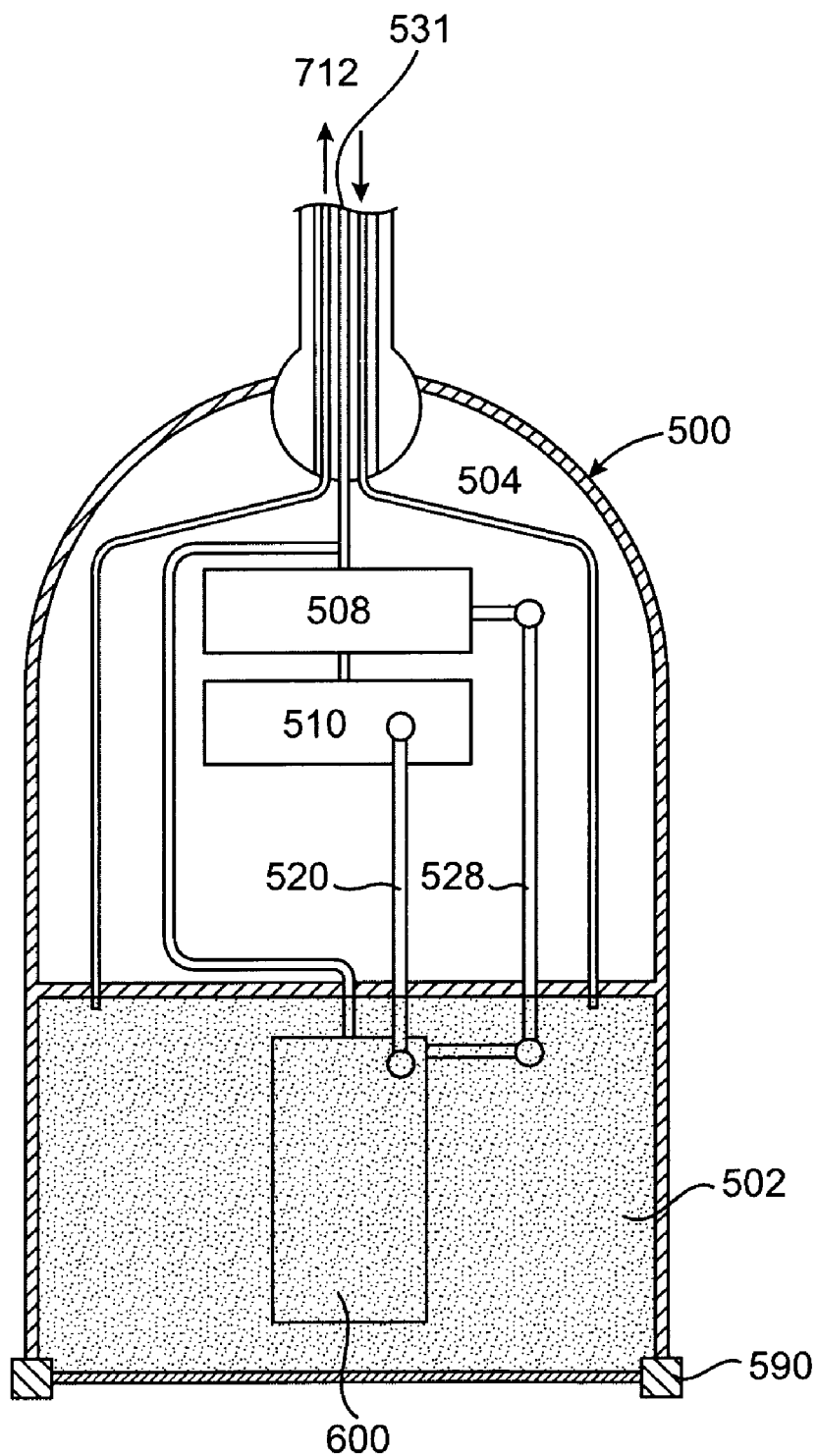
FIG. 2 illustrates a scan head.

Preferably the exterior design of the therapy head is ergonomic so a user may hold the therapy head in one hand while moving it, or orientating it against the skin surface of a patient. The ergonomic fit is for holding and guiding, but not for carrying the weight since the therapy head is intended to be supported by mechanical means. The therapy head (FIG. 2) is connected to the mechanical arm 200 by a retainer 260. From the top end of the therapy head there are a plurality of connection lines 531 used to connect the components inside the therapy head with the therapy controller 250, electronic controller (computer) 400, and the degassing system 7. The lines maintain the electronic and fluid communication between the therapy head 500 and the base unit 100.

In the principle embodiment the therapy head has an upper chamber 504 and a lower chamber 502. There is a fluid tight seal separating the two chambers, and there may be one or more pass through ports. If pass through ports are present, they are used for mechanical linkages 520, 528, electrical communication lines and possibly for fluid flow lines 712. The upper chamber 504 preferably contains a pair of motor drive units 508, 510. The lower chamber 502 contains at least one energy applicator 600. The energy applicator transmits through an aperture 590 that is transparent to the appropriate form of energy used. There is a connecting means between the motor drive unit and the energy applicator. In addition, there are a plurality of cables that connect the motor drive unit(s), the energy applicator and the fluid circuit with the corresponding elements in the base (the therapy controller and the degassing system 7).

Figure 3:
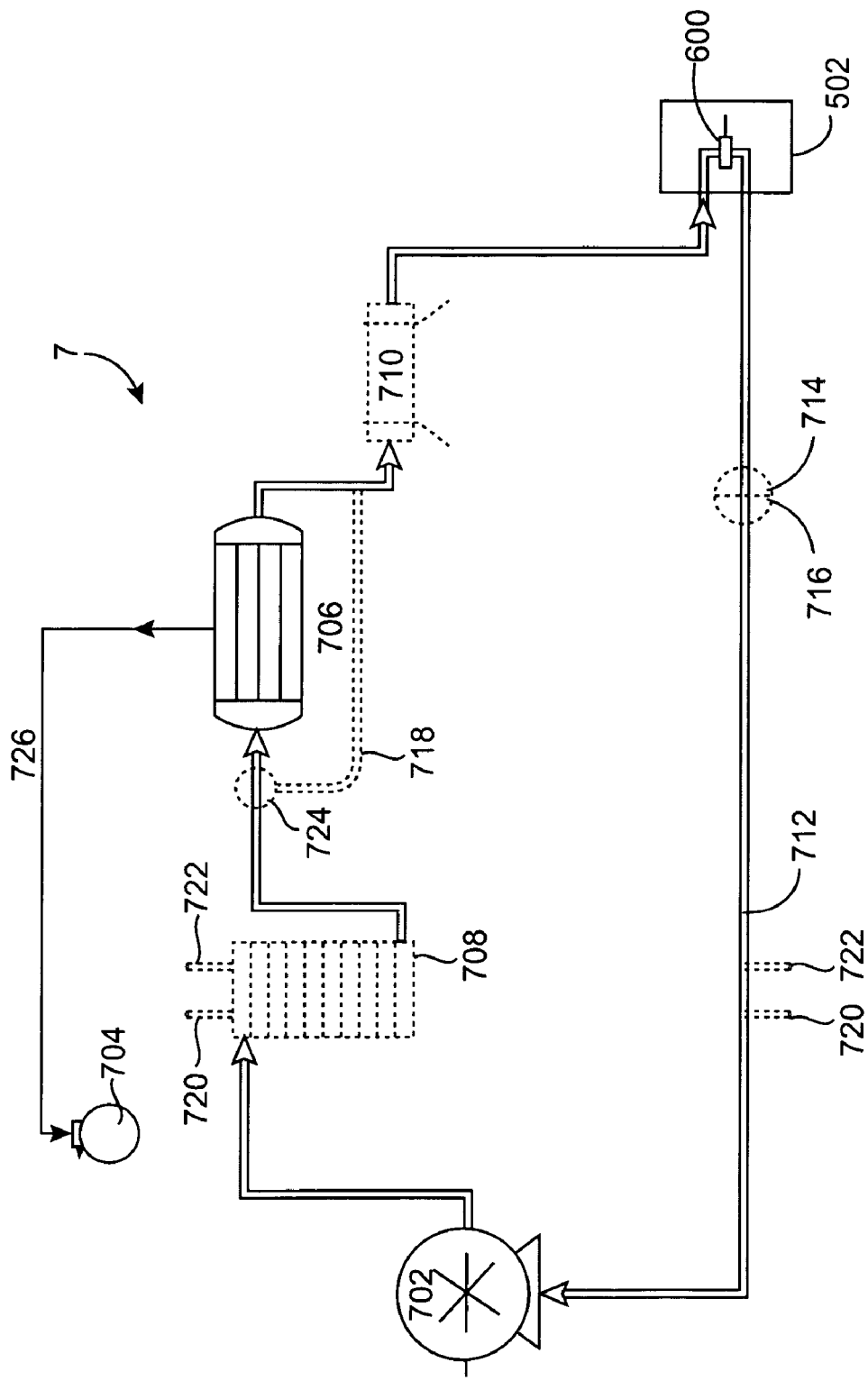
FIG. 3 shows a schematic of a degassing circuit.

A degassing system (FIG. 3) resides in the base 100 but has a fluid circuit 712 that extends to the lower chamber 502. The fluid circuit has a fluid pump 702, vacuum pump 704, vacuum chamber 706 and an exhaust line 726 for gas. Optionally the degassing system may have a fluid reservoir 708, a chiller 710, a set of input or exhaust valves 720, 722 as well as a bypass valve 724 and bypass fluid conduit 718. Sensors 716, 714 may also be used to monitor the fluid in the circuit. Fluid in the lower chamber 502 is used to help couple the transducer 600 to the patient, and to reduce any cavitation effects near the transducer 600.

The therapy head 500 (FIG. 4A) is now shown in more detail. There is an energy applicator 600 within an enclosure 566. The enclosure has a window 590 for allowing radiant energy to pass from the enclosure to a patient. The therapy head 500 is preferably small and light enough for a physician to move it comfortably with one hand. The therapy head 500 may increase in both size and weight if the physician is assisted by an articulating arm 200 in bearing the weight of the therapy head 500. There is a data link 572 extending between the therapy head 500 and an external computer 400 or a therapy controller 250. There is a top or upper chamber 504 and a lower or bottom chamber 502.

The therapy head 500 may be mounted on an articulated arm 200 supported by a base 100. The articulating arm 200 would also have its movements and functions monitored or controlled by a computer 400 or therapy controller 250.

Preferably the therapy head 500 contains motor drives 508, 510 for moving the energy applicator 600 within the enclosure. The motor drives are connected directly, or through a gear assembly (not shown), to a pair of traveler rods 520, 528. The traveler rods in turn move a pair of slotted actuators 520', 528'. The slotted actuators travel along the traveler rods carrying the energy applicator at the intersection of the two slotted actuators. As the traveler rods rotate in response to movement from the motors, the slotted actuators carry the energy applicator throughout the range of motion of the slotted traveler rods. Rotational encoders 530 are positioned on the traveler rods 520, 528 so that the movement of the energy applicator can be accurately measured.

In another possible embodiment (FIG. 4B), the motor drive units 508, 510 can be used to control a plate 534a that is magnetically coupled to a plate 534b attached to the energy applicator. The plate is moved by the motors and the energy applicator moves in response. The energy applicator is not physically connected to any sort of traveler rod or moving device except by the magnetic connection. There is still a need for a pass through port so the energy applicator remains in electronic communication with the therapy controller 250 and the computer 400. However even this pass through can be eliminated by using a short range "wireless" communication device.

The lower chamber 502 is fluid tight so a fluid coupling solution 701 can be introduced into the chamber. The fluid surrounds the energy applicator and provides coupling for the applicator to the patient. Preferably the energy applicator is a HIFU transducer. The fluid is used to provide coupling so ultrasound energy can be transmitted to the exterior of the therapy head. The coupling fluid circulates in and out of the lower chamber through a pair of supply hoses that are connected with the degassing system in the base 100. Since HIFU emissions are known to cause cavitation, and cavitation adversely effects ultrasound transmission, it is desirable to have the fluid degassed while the system is being operated. Thus fluid enters the lower chamber on one side of the therapy head and exits on the other side. A fluid current is established as fluid flows in one direction through the lower chamber, and any gas bubbles that may form during the HIFU procedure are removed instead on allowed to circulate within the chamber and potentially interfere with the procedure.

The degassing system 7 utilizes well established components and procedures for removing gasses from solution. In addition a chiller may be added to cool the fluid. Chilled fluids are less likely to form gas bubbles than warm fluids as a matter of fluid dynamics. In addition chilled coupling fluids help reduce the temperature on the therapy transducer and allow the HIFU transducer to operate for extended periods of time without heat build up. The fluid circulation system may use any fluid suitable for ultrasound coupling, so long as the fluid has a relatively low viscosity so that it may be circulated and degassed efficiently. The preferred solution is water.

The scan head or therapy head 500 may also incorporate numerous sensors on the exterior of the lower chamber. The aperture through which energy is transmitted is placed against the patient skin. During a HIFU procedure, a variety of sensors may be utilized to promote the efficient tracking of the therapy head over the patient surface, as well as facilitate the safe operation of the device. The therapy head may also have a haptic sensor incorporated into it. The haptic sensor provides pressure feedback to the user through the first control means or through a display or alert device. The sensor measures the pressure the therapy head exerts on the patient body and provides the user with either resistance feedback, or graduated pressure information to allow the user to feel the amount of pressure the therapy head is exerting on the patient skin during a procedure. The feedback can be used to give the user sufficient tactile responsiveness to prevent the robotic arm from injuring the patient. Alternatively the robotic arm may have a safety limitation placed on the resistance feedback to prevent injury to the patient, or to prevent overly deforming the skin contour of a patient during a procedure. Specifically where the medical device is or comprises a therapy transducer for treatment of adipose tissue, it is important that the tissue volume not be overly compressed or deformed to the extent that the focal zone of the transducer no longer lays within the volume of adipose tissue. Since the tissue volume is "soft" (as opposed to muscle tissue or areas having bone or hard tissue near the surface) it is easily deformed. Thus the haptic sensor is necessarily adjusted to be responsive to even small pressures on the patient skin. This allows for a stronger resistance feedback to the user with a minimum of tissue deformation.

The haptic sensor works in combination with a load sensing device that is used to keep the therapy head in contact with the patient body. The load device can be part of the robotic arm force generating mechanism, or a separate counter balance device used to counter a portion of the therapy head weight while allowing sufficient weight to transfer through the therapy head to keep the therapy head engaged with the skin surface.

A variety of tracking sensors may be used to detect and track the position and orientation of the therapy head as it moves over a patient. The position information may be stored and incorporated into a precision mapping feature if desired. A volumetric tracking program can provide real time information on tissue treated (see below).

In one alternative embodiment, the scan head has only a single fluid filled chamber. The motor assembly is either located within the assembly (using motors in fluid tight casings) or the motor assembly is outside the therapy head. In this embodiment, the motor assembly may be located opposite the therapy head on the distal arm segment 208 of the arm 200. The motor assembly may impart movement to the energy applicator 600 by a drive cable, timing belt or other mechanical device.

In yet another embodiment, the motor force may be provided by pressurized fluid pushed through a fluid driven motor, or fluid driven mechanical driver. In this embodiment, the fluid force already built into the therapy head can be used to also provide the motive force to move the energy applicator.

Figure 4A:
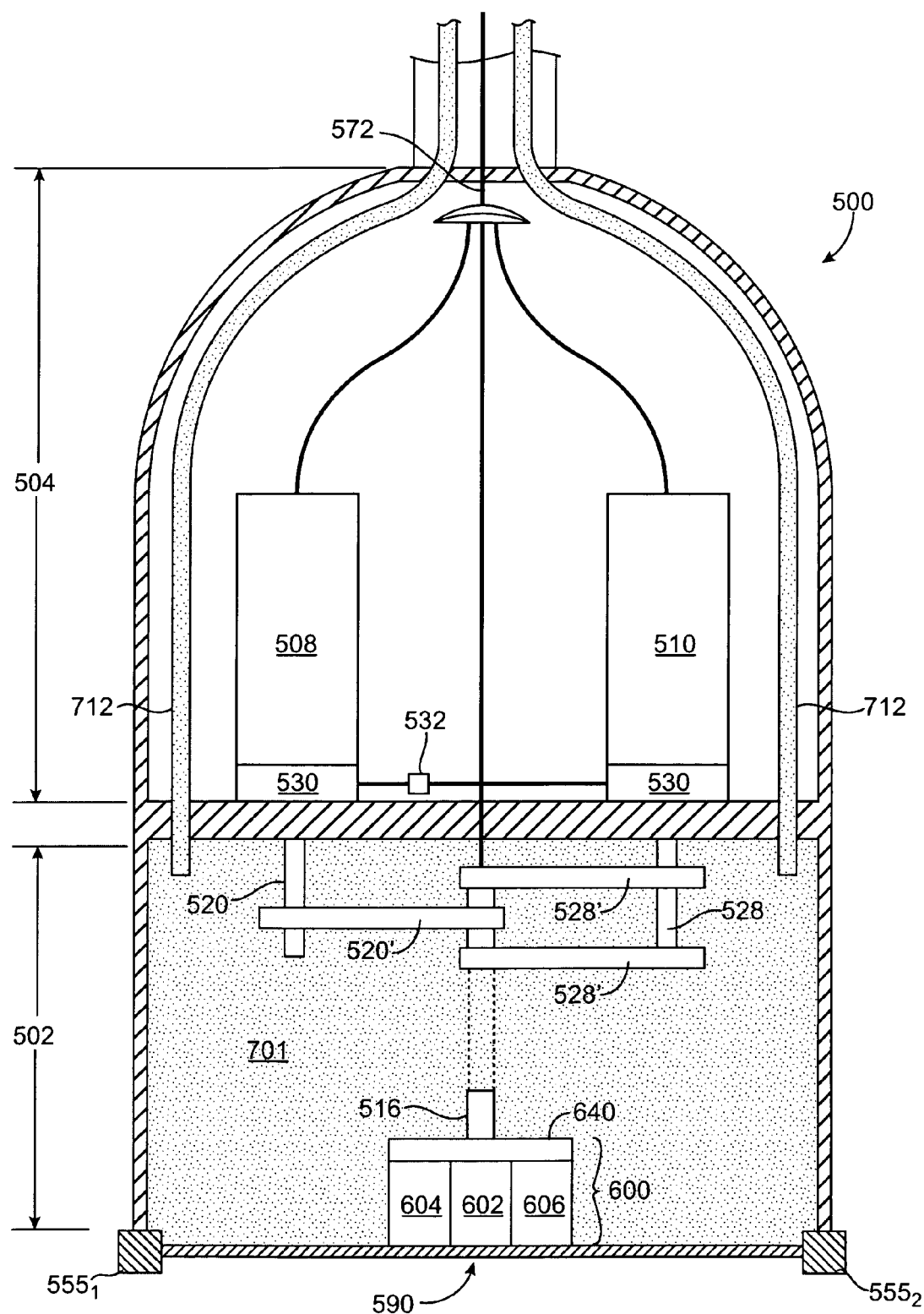
FIGS. 4A-B show elements of a therapy head.
Figure 4B:
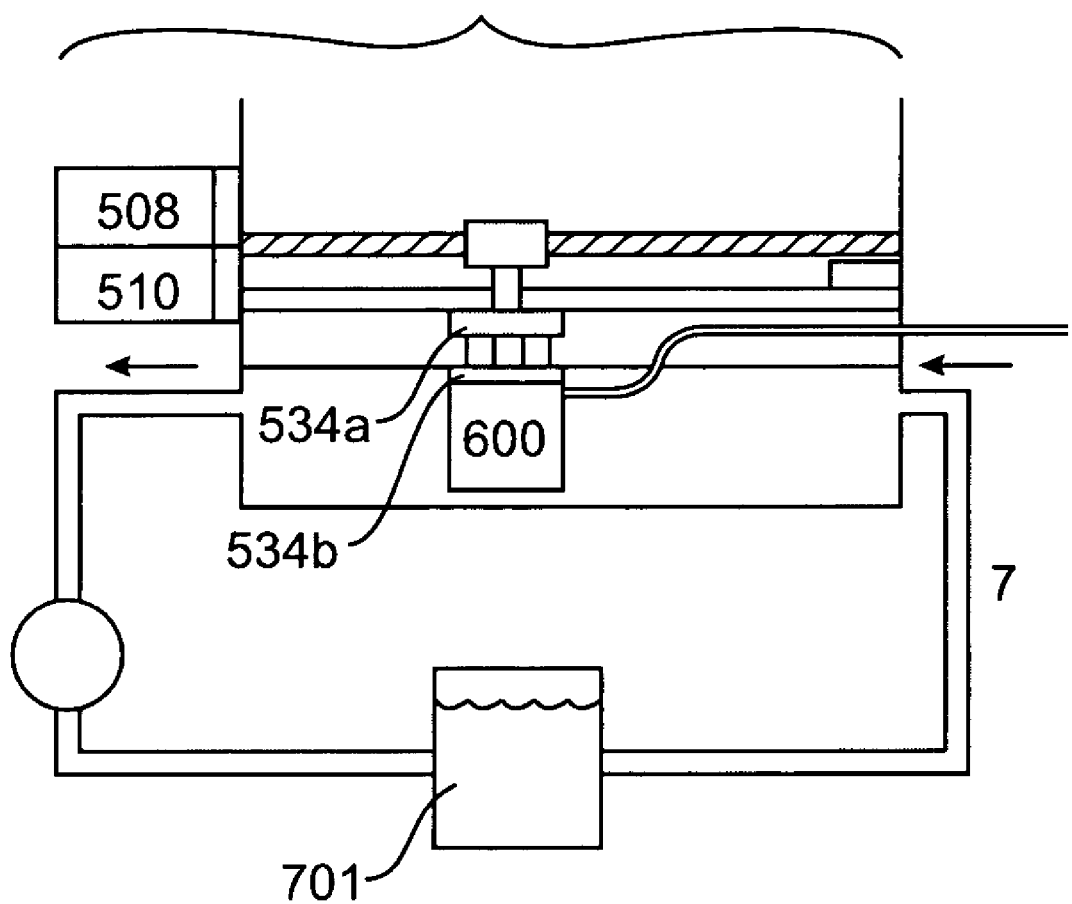

The energy applicator is preferably a HIFU ultrasound transducer having one or more diagnostic ultrasound elements that can be used for tissue scanning. The "a-line" scanner can be centered to look through the focal zone of the HIFU transducer, or can be arrayed around the perimeter of the HIFU transducer to look at tissue near the focal zone. The a-line scans may be performed before, during or after the HIFU scans, and preferably the a-line imaging is done concurrently with the therapy transducer, either interleaved with a pulse wave form of the HIFU transducer, or in the form of continual scanning through or around the HIFU focal zone. The energy applicator 600 FIG. 4A is represented by a plurality of elements 602, 604, 606 to represent multiple types of energy applicators may be combined into a single device and operated cooperatively during a therapy procedure. A transducer receptacle 640 is used to hold the many transducer elements in place in the event a component transducer assembly is used.

The HIFU transducer may operate at any range of parameters sufficient to cause cell necrosis. In one embodiment, the system of the present invention utilizes a HIFU transducer operating at a frequency from 1-4 MHz, with a pressure up to 30 MPa, using a pulse repetition frequency (PRF) of 1 KHz or greater. The transducer is moved across the skin surface of a patient at a velocity between 4-30 mm/sec. in a uniform direction. The transducer returns to one side, similar to the carriage return of a manual typewriter. The line spacing of the therapy lines ranges from 1-3 mm.

The scan head is coupled to a patient using an ultrasound coupling agent. The coupling agent can be an acoustic gel, or a coupling fluid used in combination with a circulation system inside the scan head.

If an inline degassed coupling fluid is used, there the fluid is circulated through the scan head and then back out to a main unit where the fluid may be degassed or cooled. The fluid passes in front of the energy applicator either through a cushion, or by filling a small reservoir 502 that completely bathes the energy applicator. The energy applicator then "broadcasts" its energy through an acoustic window or other transmissible window. The window may be integrated into the scan head, or it may be an attachment, such as in the form of a disposable transducer seal.

Means for Suspending the Scan Head

Arm with Position Encoders

One embodiment of a means for suspending the scan head in space is an arm with position encoders. This is an arm designed for carrying a load during a medical procedure. The arm comprises a base for securing an articulating arm. The articulating arm has a proximal end secured in a movable fashion to the base, and a distal end. There is at least one positional encoder incorporated into the arm. A receptacle is located at the distal end for carrying a scan head. There is also a means for load balancing the arm when the scan head is engaged such that the positional encoder(s) are able to track the position of the arm in real time.

One or more position encoders are used to track the movement of the articulating arm. The position encoders are preferably sensitive enough to track position changes as small as 1 mm or less. Rotational encoders are preferred and may be included in the joints of the articulating arm so that movement of each individual arm segment relative to either the base, or another arm segment, or to the therapy head, can be tracked. Rotational encoders measure the degree or angle change between the arm segments when ever the articulating arm is moved. By tracking the change in angle between the moving parts, and knowing the fixed length of each of the arm segments, the position of any joint can be determined using mathematical calculations. If the scan head or other medical device is secured to the articulating arm via a joint having an encoder as well, then changes in the angle of the joint will assist in accurately determining the position of the scan head. While rotational encoders are perhaps the most straight forward means for tracking the position of the arm, other types of encoders may also be used.

The load balancing can take either an active or passive form. In a passive form, the means for load balancing comprises mechanical structures that provide counter balancing to changes in the articulating arm position during use. The mechanical structures ensure the arm is always sufficiently balanced to minimize any movement of the therapy head due to gravity, joint slippage or hysteresis of the arm. The arm has a means for load balancing that encompasses known methods and devices for creating or maintaining force. The force generated is used for the load balancing and can be active force generating devices (e.g. any sort of motor) or a passive force generating device (e.g. a spring and counter weight, or some sort of pressure cylinder). The exact form of the force generating device or method is not particularly critical since the invention relies on force generating methods and devices that are well established in their respective arts.

The arm is attached to a weighted base having sufficient mass to anchor the arm regardless of the position and angle the arm is moved to when the therapy head is attached. Thus the arm may be at its maximum extension and at an angle to cause the maximum shift in the center of gravity, however the base shall be sufficiently weighted or anchored such that the arm will not tip over or become unstable. The joint used to attach the arm to the base allows rotational movement of the arm relative to the base, and/or inclination and declination of the arm relative to the base. The joint between the base and the proximal end of the arm includes a load balancing device in the form of a passive or active force generating device(s).

The arm comprises two or more segments, and a load balancing mechanism is used between each segment either independently (each segment is self balancing with respect to the other segments of the arm) or dependently (each segment balances in combination with one or more adjacent segments). Load balancing for the distal most arm segment must also adjust for the therapy head and any positional changes it may create during a medical procedure. It should be self evident that in order to maintain the load balancing feature the weight of the therapy head attached to the distal end of the arm must not exceed the weight compensating ability of the load balancing means. Similarly the range of motion of the arm itself should be restricted to prevent the arm from becoming unbalanced. The load balancing mechanism should compensate for both the load of the therapy head and the change in the center of gravity as the therapy head is extended away from the base in a horizontal plane (the most unbalancing configuration). Preferably the load balancing mechanism also compensates for any hysteresis that may accompany the movement of the arm. Thus the greater the ability of the load balancing mechanism, the greater range of motion allowable on the articulating arm. Using the encoders of the arm to determine position it is possible to control the range of motion of the arm depending on the weight of the therapy head. The therapy head itself may provide data to the articulating arm in the form of a data chip which can be read by the arm. The data chip may contain information as to the mass of the effector or therapy head, as well as to its operational design. That is too say, each time a new therapy head is attached to the distal end of the arm, the movement controller of the arm is "smart" and can figure out what range of motion will be allowed. Thus range of motion limitations or "stops" can be implemented on the arm using either the load balancing device in the case it can be electronically controlled, or the controller can issue a warning when the range of motion is approaching the acceptable limit. Such warning may be an audible tone, warning light or other signal easily communicated to a user. Alternatively a mechanical stop can be set either manually or automatically to physically inhibit the movement of the arm beyond the balanced range prior to the beginning of a medical procedure.

The data generated by the encoders are relayed to a controller. The controller is a computer device used to provide the apparatus with a position tracking device or a closed loop control mechanism. In passive mode, the controller does not provide active force to the articulating arm, instead it provides a signal to a user as to where the arm should be moved, or should not be moved.

In the passive mode, the load balancing means can be simple weights and springs running inline with the articulating arm so that the movements in the arm will produce a corresponding change in position of a weight and/or spring or in the arm itself if desired. One can visualize a four bar arm as an example. The use of an independent passive load balancing mechanism is preferred. In this manner each arm segment balances simultaneously with all other arm segments when the arm is moved.

In a dependent passive mode, a series of springs and weights may again be used, however it would be more efficient to use a series of gas, hydraulic or pneumatic motors designed to relax when pressure is applied to the distal end of the arm (or therapy head) or in response to the activation of a trigger mechanism. Pressure or force from these passive force generating devices is re-established once the arm has been manually placed in a desired position. The pressure or force on the arm segments prevents the arm from moving again until an operator releases the standing pressure or force.

In yet another embodiment, an active load balancing mechanism can be used using any kind of active force generating device (such as air/hydraulic cylinders or pneumatic motors). These can operate either independently or dependently based on the commands provided by a user through a robotic driver. An advantage to the active load balancing mechanism is the way the articulating arm can compensate the positioning of the arm automatically during a procedure while leaving the therapy head in the desired position. For example, when a user wishes to change the roll, pitch or yaw of the therapy head to match the local contours of the patient body, this may be done by moving the therapy head within the joint used to connect the scan head to the distal end of the arm. Changes in the orientation of the scan head can cause minute or significant changes to the balance of the articulating arm depending on the size and weight of the scan head. Using an active load balancing mechanism, the robotic driver can adjust for the changes in the scan head orientation without changing the position of the distal end of the arm.

The position encoder of the present invention may be mechanical or optical encoders included incorporated into the arm itself, or it can be one or more feedback devices that are used external to the arm. Alternative embodiments of the encoder include using one or more optical devices for tracking the position of the arm as it moves. The arm would incorporate a plurality of optically readable tags that the sensors could readily identify and track. Another alternative is there can be a single RF transmitter at the tip of the proximal end, and an RF receiver located in the base, or in a fixed location externally. The RF data would allow the controller to track the movement of the distal end and know where the effector is positioned. Such embodiments, and any equivalents, are not considered as preferred embodiments, but are still well within the scope of the present disclosure.

The controller may be a software application or hardware device (or combination of the two) that receives the data from the encoders and calculates the position of the therapy head. The controller can also calculate the position of each individual segment of the apparatus, and map the movement of the apparatus in space. Since the encoders are in electronic communication with the controller, the data for knowing where the therapy head occurs essentially in real time. The delay in computer processing of the data is minute and too small an interval for a user to detect. Even in the course of doing a medical procedure, no procedure that is currently manually conducted by a physician would experience any noticeable or operable delay using the present invention.

In addition to calculating the position of the apparatus in space, the controller can provide movement information to the arm by acting as a robotic controller for any actuated control components of the apparatus. The controller can also receive data from an external feed, or read information from a data file. In this manner the controller can act as a robotic controller to follow real time commands from a user or another computer, or read a data file that provides a map or series of movement commands that the therapy head must follow. Furthermore if the therapy head requires precise activation at particular coordinates, the controller can handle these operations as well.

The distal end has a therapy head attached to it. The attachment must be secure, but should also be removable so that the therapy head can be removed between procedures, or interchangeable for different procedures. The range of motion between the therapy head and the distal end of the articulating arm can likewise be determined using a rotational encoder in the joint connecting the therapy head to the articulating arm. The joint between the therapy head and the articulating arm may have multiple rotational joints, or a ball joint to allow greater mobility of the therapy head. Encoders in each joint, or an encoder capable of accurately gauging the change in angle in a three dimensional joint, provides the needed information to determine the exact position of the therapy head. Similarly, once angle and distance from the base are determined, it is a simple matter to include any additional information such as the length of a particular medical device from the last encoder in the chain going from base to distal end, and thus determining the exact three dimensional coordinate position of the effector or therapy head.

Alternatively, the robotic articulating arm may constructed following the same guidelines above, or it may be a large device. Again the base is anchored to the floor or a wall, or a table top. The procedure and the types of medical devices used would dictate the size of the robotic articulating arm. Medical devices requiring a more robust support structure would naturally require an arm having a greater load bearing ability, and a greater stability factor incorporated into the base. Smaller devices could use an arm that could be portable and anchored to a table top surface using clamps or similar means.

Load Balancing Arm without Position Encoders

Similar to the load balancing arm previously described, the therapy head may be suspended in space from a load balancing or robotic arm without the benefit of position encoders. A manual varient of the arm is herein described where the arm provides the load carrying ability previously described, without the position sensing and tracking capability. Such an arm is both easier to manufacture and produce, and easier to maintain, however it lacks the precision of the previous embodiment.

The arm without position encoders can be used primarily as a load carrying device, relieving the user from bearing the weight of the therapy head. However the user must take the responsibility for moving and positioning the therapy head while simultaneously keeping track of the area that the scan head has previously treated. The arm shown in FIG. 5 shares many of the elements previously described. The arm 200 has a base 100 and a plurality of arm segments 204, 206, 208. The arm 200 is secured to the base 100 via a platform 202 and has a plurality of tensioning devices 234, 236, 238 for maintaining the position of the arm when moved. The therapy head 500 is seated in a retainer that can swivel relative to the distal arm segment 208. A user may manipulate the position of the arm by using the therapy head as the control means. A user can grasp the therapy head and move the therapy head in space while the arm supports the weight of the therapy head and keeps the therapy head positioned where ever the user desires it. In this embodiment the arm lacks the ability to correct the position of the therapy head in accordance with any position that may be provided through the therapy controller. Instead the user will have to maintain the proper positioning. Alternatively, one of the arm segments bearing the primary load of the therapy head 500 may use a counter balance 238' instead of the force generating device 238.

In this embodiment the robotic force generating devices are replaced with tensioned force generating devices. These offer sufficient resistance to over come joint slippage, hystereses and gravity, but are pliant to additional force application such as when the user applies force to move the therapy head. Once the added force is released, the tensioned devices maintain the position of the therapy head.

Guidance System for Arms

The guidance system for the therapy device positioned on the robotic arm is preferably made of two components working cooperatively. The first control means provides a "macro" level of control to the therapy device, by controlling the movement of the robotic arm. The second control means provides a "micro" level of control to the medical device within the therapy head.

Figure 5:
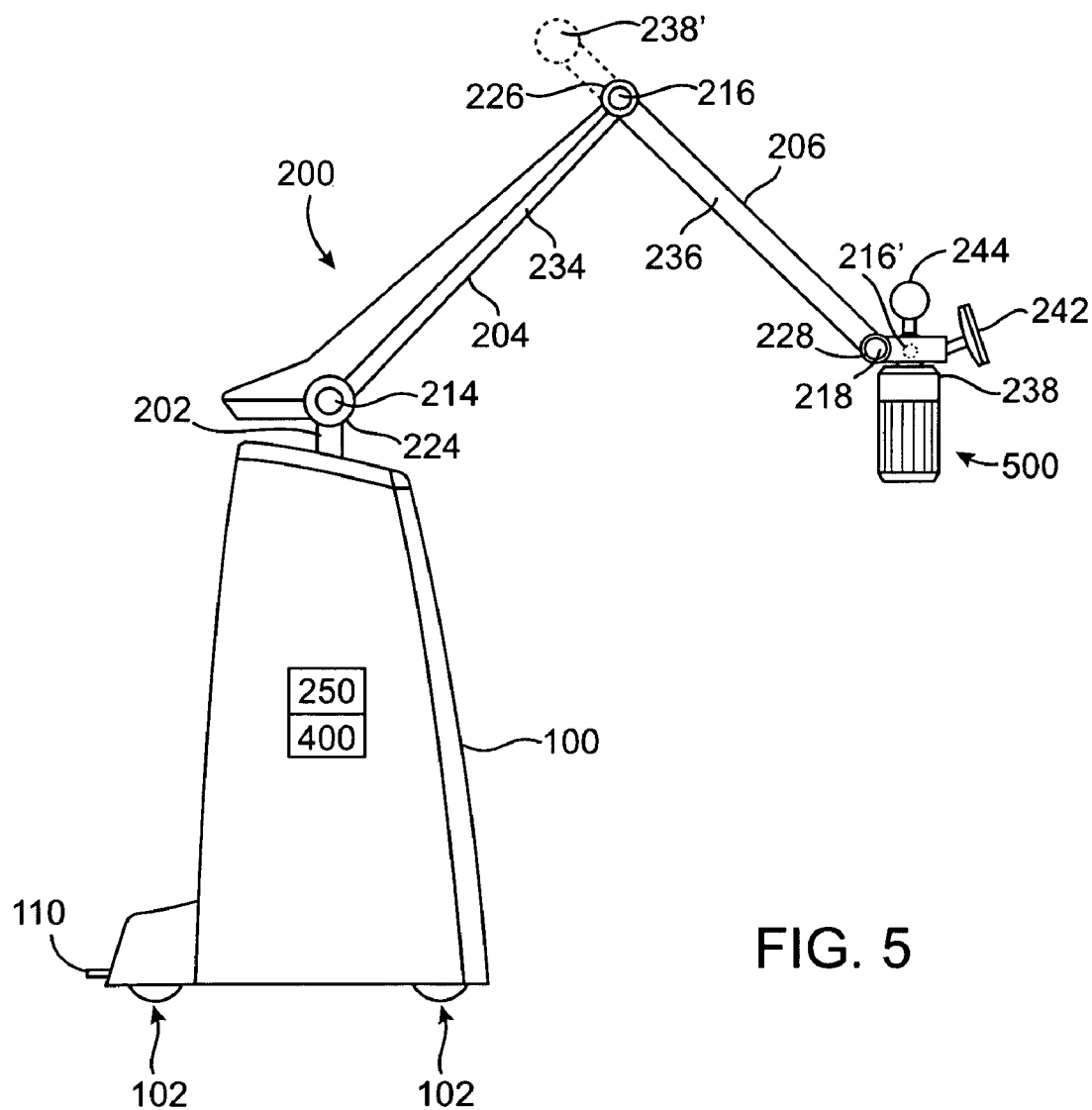
FIG. 5 shows an arm with a computer like input device.
Figure 7:
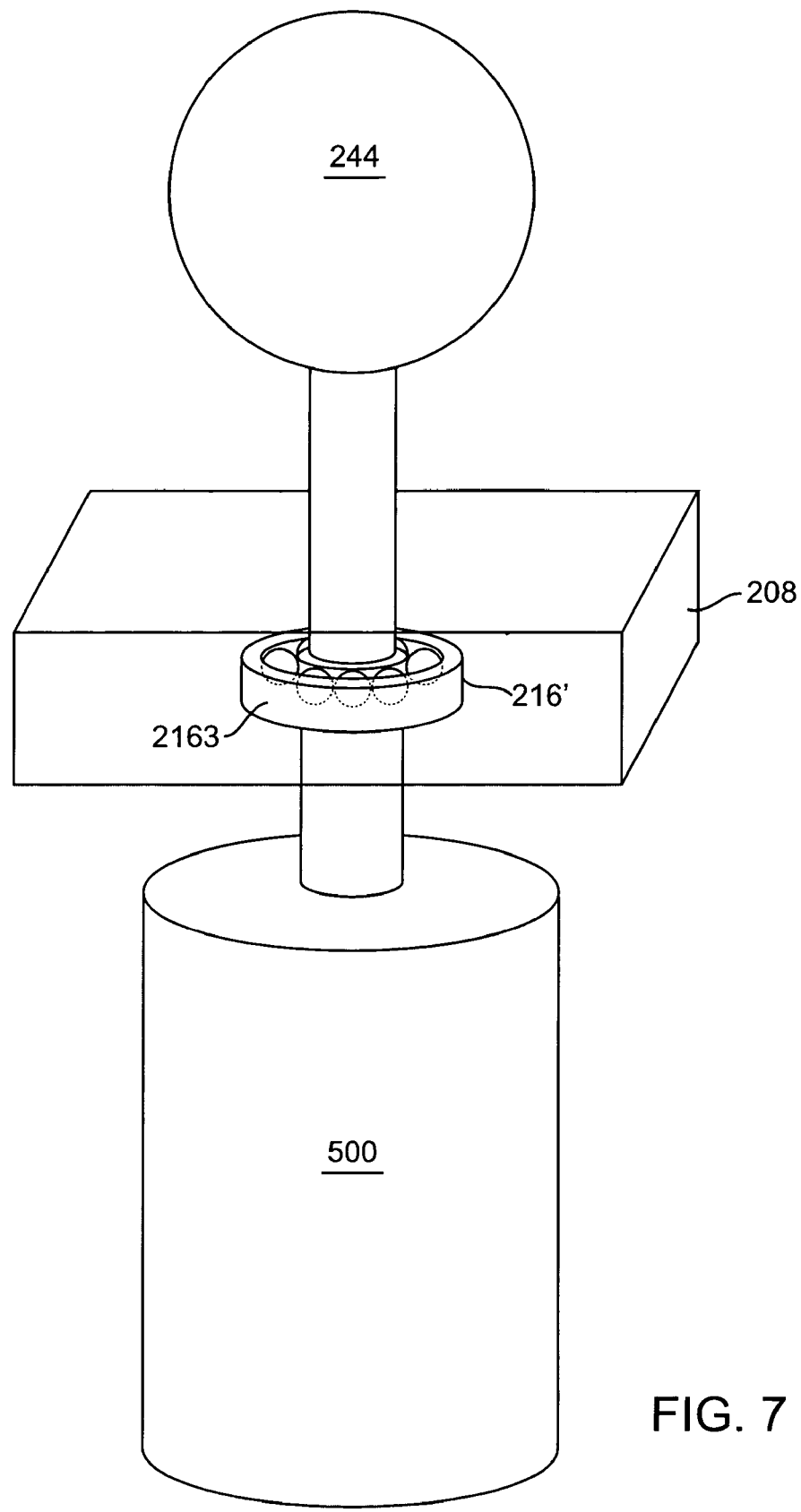
FIG. 7 illustrates a slip joint.

Command and control of the robotic arm is provided by a first control means (FIG. 5). The system shown has the same elements as previously described with the addition of a computer like input device 244 mounted on the distal arm segment 208. There is also an optional slip joint 216' (FIG. 7). The first control means 244 provides movement instructions to the motors or other force generating means of the robotic arm. In addition to movement instructions for the robotic arm, the first control means can also provide virtual position information to a user through a visual display 242.

The first control means may be a variety of different devices capable of guiding the movement of the robotic arm. In a first embodiment of the first control means, a computer input device can be used to provide both virtual positioning of the therapy head, and movement instructions to the robotic arm. The computer input device may be any of a class of input device normally used to provide movement commands to a pointer (cursor) on a computer screen. These are in general two dimensional input devices such as a mouse, tablet device or trackball. In addition three dimensional input devices can be used to provide virtual positioning in a three dimensional visual frame on a computer screen. Such devices are commonly exemplified in joysticks, D-controllers and the like. Finally true freedom on movement in a virtual environment can be provided by a six degree of freedom (DOF) device, such as a "spaceball" input device commonly used in Computer Aided Design (CAD) applications. The input device used as the first control means may be an off the shelf type of computer input device, or a specially designed device to operate with the robotic arm. The device used for the first control means may be interchangeable, so that depending on user preference or medical procedure requirements, a different input device may be used from one procedure to the next, even when using the same robotic arm.

Although it is preferable for the robotic arm and the input device to have the same DOF, it is not essential. The input device used for the first control means may be interchangeable. That is to say it is not necessary that the input device be either permanently or fixedly attached to the robotic arm. The input device may connect through a computer connection interface such as are commonly used for computer input devices. Thus one input device may have three DOF while another has six DOF, yet both are adaptable to command and control the robotic arm through a common interface port. Ideally the robotic arm has six DOF through the therapy head, and has sufficient mobility and extension to allow the six DOF to be conveyed to the therapy head without physically interfering with other objects present during a medical procedure, such as the patient or the user.

The movement of the input device produces movement instructions in the same way as a computer input device produces virtual location information for a cursor or other virtual object to be displayed on a computer screen. However in addition to the virtual movement and location information provided by the input device, the movement information is also translated into actual movement commands for the motors or force generating devices used to control the robotic arm. In this manner the use of a computer input device allows a user to manipulate a potentially heavy and cumbersome medical device with no more effort than is needed to operate a computer input device. Unlike some computer input devices that are of fixed orientation (such as I-beams or cursor arrows), the orientation of the cursor displayed on the computer screen for the input device described herein preferably corresponds to a known orientation of the medical device. For instance the cursor arrow may point in the same direction as the medical device emits energy, or in the opposite direction. Thus movement of the input device, and changes in the orientation of the cursor in a virtual environment will produce a corresponding change in the position and orientation of the medical device or therapy head.

Similar to a normal computer input device, the input device used with the system of the present invention may have buttons or scroll wheels or other actuators on them that may be programmed to correspond to particular operable elements of the system. For example the buttons on the input device may be used to toggle between turning the motor of the robotic arm on or off, activating the medical device either to perform a therapy treatment or refresh some sensor data.

An important distinction in the application of input devices to the present disclosure with the general application of such devices is the repositioning aspect of such input devices. It is perhaps common knowledge that a computer input device may be repositioned with ease to compensate for ergonomic desires of the user. For instance a mouse or joy stick may be picked up and moved while the virtual position of the mouse pointer, I-beam and the like remains the same. This advantage of the computer input device can be adapted to the input device used as a first control means for the robotic arm within certain limitations.

The advantage can be translated into control of the robotic arm where the movement of the therapy head, medical device or robotic arm is also suspended while the input device is being repositioned. However the advantage cannot be translated where the input device is being used to trace over a path that is either an actual placement of the therapy head, medical device or robotic arm in relation to the patient (see below) or a representative depiction of the position of the therapy head, medical device or robotic arm with respect to the patient body.

A representative placement involves either a map or a model of the patient skin surface to be used instead of the actual skin surface. In one alternative embodiment of the tracking system, a map can be created of the patient skin surface using a projection image and a camera. A projector casts an image on the patient body of regularly spaced gridlines, or grid squares. The lines are projected from a template, the template having a known line spacing. The line spacing may be regular or irregular so long as the distance between each line is known. The projected line image falls on the patient surface where it can be detected by a camera at an angle off the projection line. The camera reads the distances between the lines producing a second distance value for a side of a right triangle. Thus using simple trigonometry, the elevation distance between lines can be determined.

A tracking system can follow a two dimensional image of the projected map, wherein the actual distances on slope surfaces is determined by mathematical calculation rather than from direct measurement. In this manner the two dimensional map provides a good approximation of the distances and slopes and allows the ultrasound system to adapt to the longer (or shorter) slope distances and transmit the appropriate level of energy.

Similarly in another embodiment of the tracking system, a three dimensional representation of the patient can be used. The three dimensional representation can be a contoured dummy, or a cast derived from the body of the actual patient. The three dimensional need not be large or precise so long as it is large enough to encompass the desired treatment area, and accurate enough so that the focal zone of the transducer that will track over the actual patient body, does not project into muscle tissue or other tissue that should not be treated.

In either of these tracking system embodiments, it should be appreciated that it is both desirable and beneficial to maintain sufficient accuracy in the model or tracking system using a proxy for the patient skin surface, that the actual therapy device continues to treat only undesirable adipose tissue. A imaging or a-line scanning transducer can be used to ensure therapy is applied strictly to adipose tissue during a therapy session. This permits the detection of adipose tissue in real time, and provides a detection means for the system to be shut off, or shut down in the event the imaging sensor detects non-adipose tissue. Even if the user feels the therapy head is over the proper adipose tissue zone, the device itself has a safety back up.

In an actual placement situation, the repositioning of the input device would similarly be undesirable for the same reasons above, except the repositioning of the input device would correspond to a direct change in the placement of the medical device, therapy head or robotic arm.

The computer input device used as the first control means may be directly mounted on the robotic arm. Preferably an input device having six DOF would be mounted in this case, and located substantially near the therapy head. A user can operate the input device by manually manipulating the input device (such as a joystick or spaceball) and seeing the movement commands of the input device translated into the movement of the robotic arm. The user is thus "in the loop" as far as control and guidance of the robotic arm is concerned and can make decisions for the angle and positioning of the therapy head without the need to examine a display screen having a virtual representation of the movement of the robotic arm. The user may make adjustments to the positioning of the therapy head in all six DOF while being a user in the control loop of the robotic arm.

A visual display device 242 may be mounted on the robotic arm so a user may manipulate the therapy head 500 while still looking at the display device 242. In this manner a user can evaluate sensor information and data on the display while simultaneously using the input device to guide the movement of the medical device, therapy head or robotic arm. The data provided by the sensor(s) are displayed on the screen and allow the user to manipulate the input device to maximize effectiveness and safety of the medical device or therapy head without being forced to look in several different directions to gather the information needed to guide the system.

Figure 6:
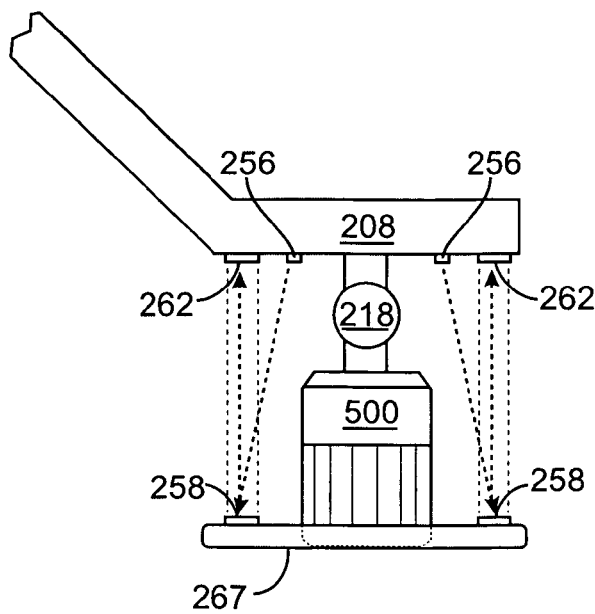
FIG. 6 shows an optical guide ring control device.

In an alternative embodiment, the first control means may be a guide ring 267 placed onto a patient body (FIG. 6). In this embodiment, the guide ring 267 provides targeting data, and there is a tracking system incorporated either into the robotic arm 200, or into the therapy head 500 (or having elements in both). For illustrative purposes, the guidance system may be an optical tracking device that emits light from emitters 256 on the robotic arm 200. The light is reflected off reflectors 258 on the guide ring. The reflected light forms a pattern or orientation that optical detectors 262 positioned about the therapy head 500 are able to read. The optical sensors 262 thus can determine where the center of the guide ring 267 is, and provide movement and orientation command instructions to the robotic arm so that the robotic arm moves to keep the therapy head centered within the target ring.

The target ring is either transparent in the middle, or has an aperture. The aperture or transparent material must not significantly interfere with any energy the medical device may emit, nor with the sensors that may be incorporated into the medical device. The ring may be made of a pliable material so that when placed against the patient body, it conform to the contours of the patient, or it may be rigid so as to provide a definitive plane of reference for the user and/or therapy controller. The user of the system may manually move the target ring along the surface of the patient body while the tracking system follows the movement and angular changes in the target ring. The tracking system provides the appropriate command and control information to the robotic arm and the therapy head is moved so that the medical device, remains as much as possible, centered within the target ring, and angles so the medical device is perpendicular to the general plane of the target ring.

Alternatively the user may place the target ring onto the patient in a single place, and permit the micro controller (the second control means) to treat an area within the center of the guide ring.

The target ring may be manufactured having one side adapted for smooth gliding over the patient body. It may be treated with a silicon or polymer material to reduce friction of the device as it moves over the patient. The side facing the tracking system (facing away from the patient body) has sufficient visual cues or markers on it to produce an asymmetric reflection or refraction image. In this way the tracking system will be able to determine a direction of facing, and rotate to adapt to the rotation of the target ring so the medical device or therapy head is properly oriented at all times.

Figure 5A:
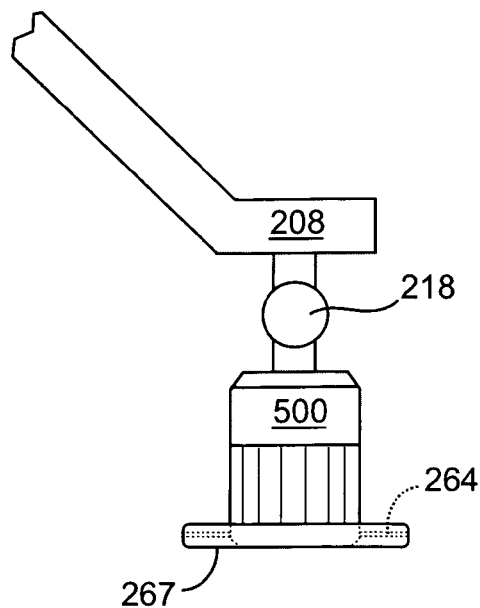
FIGS. 5A-B illustrate a guide ring control device.
Figure 5B:
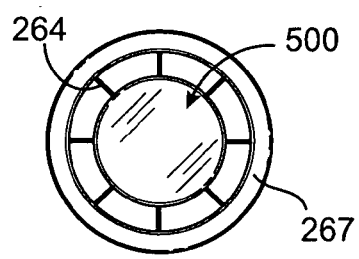

The target ring 267 may be physically joined to the therapy head 500 by using wires or similarly capable strain gauges 264 around the perimeter of the therapy head and connected to the target ring (FIG. 5A-B). The movement of the target ring 267 over the patient body produces strains in the wires or strain gauges 264 that the electronic controller 400, 250 can detect, and correspondingly move the therapy head 500 in response to reduce the strain. In this manner the therapy head can follow the target ring using a physical connection. Alternatively the therapy head may have a magnetic coil with the target ring having a similar magnetic field. Changes in the strength or charge of an electromagnetic field allow the system to detect the movement and direction of the target ring and compensate accordingly by moving the therapy head in response.

Alternatively, the tracking system can be made to follow a detectable path traced or imprinted onto the patient body. In this embodiment, a user or operator may set the therapy head onto the patient body (either in physical contact, or in close proximity to the patient body). The tracking system thus serves as the first control means and automatically follows the path on the patient body. The second control means may be an input device a user can control to provide micro-control of the position of the medical device while the therapy head is tracing a path over the patient body. Alternatively, the electronic controller or therapy controller may have a program that serves as the second input device for moving or oscillating the therapy head or medical device. This movement or oscillating would serve as a "wobble" like effect that would sweep out an area under the patient skin that the transducer was focused on while the tracking system is operating.

Fiducials may be placed on the patient skin for the tracking system to follow. It is not necessary for a path to be drawn on the patient body for the tracking system to follow if the electronic controller has a program or designated response for tracking over a surface area defined by discrete fiducials. In this case, the first control means can be used to bring the robotic arm and therapy head into position within an area defined by fiducial markers. The second control means can then take over and move the therapy head within the fiducial markers according to its program parameters. The software program that guides the movement of the medical device or therapy head becomes the second control means. Where the surface area to be treated is large, the first and second control means may operate cooperatively simultaneously. That is the user may guide the robotic arm while the therapy program operating as the second control means handles the movement of the medical device within the defined treatment area.

Yet another embodiment combines the tracking system with an input device so that a user can use the input device to manually direct the robotic arm, therapy head and medical device to follow the path traced out on the patient body. Once again the second control means may be an automated path adjustment instruction providing an artificial wobble to the movement of the therapy head as the robotic arm traces out the path on the patient body.

Still another embodiment calls for the use of a customized input device of similar design to a computer input device, but being incorporated into the robotic arm during construction. In this embodiment, the control means is integrated into the distal end of the robotic arm substantially near the therapy head. The integrated first control means utilizes technology similar to those of computer input devices such as optical tracking elements, strain gauges, force and torque converters and the like. However the input device is built having the same DOF as the arm, and it positioned for the ease of use of the user.

The second control means provides movement command and control of the medical device within the therapy head. The second control means is used where the therapy head has a micro-motor assembly, or other force generating means for the movement of the medical device within the therapy head itself. In this manner the robotic arm can be commanded to move the therapy head into a desired position or location relative to a patient body, and the second control means can be used for the precise placement of the medical device. Thus the first control means provides a "macro" level of control while the second control means provides a "micro" level of control.

Alternatively the second control means can be a software program that provides movement instructions to the micro motor assembly within the therapy head. Thus the precise placement of the medical device during a medical procedure may be left to an automated system. This enables the system to place the medical device in precise locations, for precise time intervals, in response to either pre-established parameters, or in response to real time sensor data.

In another alternative embodiment of the second control means, an automatic steering variation or "wobble" can be incorporated into the movement instructions relayed from the first control means to the robotic arm. In this manner the first control means still provides the "macro" level movement commands, but an automatic variation provides for some "micro" level of movement command that cannot be imitated or implemented through the direct translation of the movement directions received from the first control means.

In still another embodiment, the input device used as the first control means can be switched between a macro guidance mode and a micro guidance mode. A switch can be used to toggle between the modes, allowing a user to interact with a single input device and have both the first and second control means available. In operation a user can use the input device as the first control means to provide macro positioning of the robotic arm and placement of the therapy head or medical device. Once the therapy head is in the vicinity of the area to be treated, as best as can be determined by the macro level guidance, the user can toggle to a micro level of control. The input device now becomes the second control means for the fine control of the medical device within the therapy head. Alternatively, fine motor controls attached to the main force generating means used for the robotic arm can provide the micro level control while using the same force generating device. This is analogous to the coarse and fine focus found on a light microscope. The application in the motor usage of the robotic arm would be one of controlling fine mesh gears versus ordinary gears, or fine versus coarse force generating elements.

The robotic arm may also have positional or movement encoders built into it. Encoders are used to track the position of the therapy device, and the movement of each arm segment during the use of the system. It may be preferable for the robotic arm to have a teaching mode. The teaching mode can be used by an operator to manually guide the arm through a desired set of movement operations. The electronic controller can "observe" the movement of the arm and memorize the starting position, final position and path taken between the start and final position. The motion can be memorized by the electronic controller and repeated as often as desired by recalling the movement instructions. Multiple movement paths may be stored if desired in computer memory.

In the embodiment where the input device is mounted to the arm, a slip joint (FIG. 7) may be incorporated in the arm to help isolate some amount of excess force or torque used on the input device from effecting the movement position of the robotic arm. The slip joint is designed to help absorb or reduce excess force. For example, rotational force may be expended on the input device to cause the therapy head to change its axial rotation. If the user exerts too much rotational force, the input device may be pushed to a physical or artificial stop. At this point the excess rotational force may be spent in the slip joint. The rotational axis of the input device may be mounted in double ring bearing assembly 2163. Once the input device reached its stops, the additional force over comes a threshold force level and allow the platform to spin within the double bearing ring. Thus extraneous rotational force is harmlessly expended. The slip joint necessarily has a pass-through for data information to be communicated from the input device to the electronic controller. The slip joint may also include a physical aperture serving as a pass through for any physical connection to the arm, or from the input device to the therapy head.

In addition to the double bearing ring 2163, the slip joint may include additional axis in which forces can be absorbed so as to isolate the arm from unwanted forces. In this manner rotational and torque forces in multiple planes can be dampened to protect the accuracy of the robotic arm. Forces that exceed the maximum force the input device can absorb, and which are not neutralized by the slip joint, would be limited by the robotic arm. The robotic arm can sense external forces (those not originating from the instructions received from the input device) and compensate for them by applying opposite forces. This "station keeping" can be useful in tortuous environments where the user is aggressively handling the input device to try and position the therapy head properly.

The DOF of the first control means may be separated into elements that are robotic, and elements that are manual. The robotic arm may be constructed with any number of DOF while the therapy head is manually adjusted for the remainder requirement DOF. E.g. if the robotic arm is constructed with three DOF, and the first input device is a computer input device having three DOF, then the therapy head may be mounted on a joint allowing three additional DOF that are not provided by the robotic arm. The tracking system would still follow the location of the medical device compiling both the manual and the robotic DOF elements into a single spatial location for both visual representation and medical procedure tracking purposes. Such a system may have the therapy head mounted axially to an input device, wherein the robotic arm can be adjusted through the input device while the therapy head may be simultaneously "aimed" manually.

Note that the use of a manual addition to the control means may be a component of either the first or second control means. If the therapy head has micro position motors for the movement of the medical device within the therapy head, the manual contribution to the DOF of the therapy head would be a component of the first control means. The first component in this case would be the command and control of the robotic arm. Here a user may use the therapy head itself as the input device to steer the therapy head and the robotic arm. The micro position control would remain with the therapy controller or the electronic controller and move the energy emitter within the therapy head. Alternatively if the medical device is fixed within the therapy head, then the manual contribution to the DOF would constitute the second control means while the command and control of the robotic arm would remain exclusively the first control means. Here the manual positioning takes the place of an automatic adjustment to the robotic path or artificially induced wobble.

It is not required the first input device be positioned in close proximity to the therapy head. The first and second control device may be positioned further away from the therapy head. For example where the robotic arm and therapy head are intended to be operated remotely, then the control means may be positioned near a remote computer with the user following a visual or virtual representation of the movement of the therapy head over the patient body. This alternative embodiment is reserved for unusual medical procedure where it is not desirable for the physician to be in close proximity to the patient body.

The moving means or motor of the articulating arm should have a rate limit such that the arm is not prone to any movements that would cause harm to the patient or operator. The movement controller thus would control the speed of both the end effector repositioning, but also the speed at which any single segment of the arm would move through space, thus avoiding or at least reducing the possibility of catching an operator or observer unaware.

Optionally a display device 242 may be positioned near the distal end of the arm 208 providing visual feedback and information display to a user during a medical procedure.

Therapy Controller

An electronic controller is used to coordinate the functions of the various elements of the system. The electronic controller can be one or more computers, or other dedicated electronic device adapted for use with the present system. The electronic controller receives the input information from the first control means, whether it is a computer input device, guide ring or tracking system. The electronic controller then translates the input information into movement instructions for the robotic arm. A second data path may be implemented which also provides for a virtual visual object to be represented on a display device. The data streams of the movement and display data paths must properly correlate so that the movement and visual representation of the movement of the system accurately coincide.

The electronic controller must also coordinate the inputs of the second control means. If the second control means operates simultaneously with the first control means, then the electronic controller must coordinate their movements so that the medical device passes over the treatment area of the patient body in a manner in accordance with the medical procedure being performed. It is imperative the electronic controller accurately compile the movement commands of the first control means and the second control means so that there is no danger to the patient. If the second control means operates in a separate time frame from the first control means, then the electronic controller merely needs to ensure that the command and control of the medical device position is being properly controlled from the appropriate controller. Similarly, the electronic controller must ensure the safety to the patient body by preventing unauthorized or inappropriate movement of the medical device over the patient body.

The electronic controller may act as a therapy controller. If a computer is used as the electronic controller, it may have the ability to execute either preloaded software that can function as a controller for the medical device, or it may have an expansion slot such as a PCI bus interface that can accept one or more boards that operate as the therapy controller. It is advantageous but not essential for the electronic controller of the present invention to be in intimate electronic communication with the therapy controller of the medical device to ensure the movement and physical placement of the medical device and therapy head is done in accordance with the therapy procedure.

The second control means may be a physical device used to provide input, such as a secondary computer input device, or the first control means after being toggled to provide fine position control. Alternatively the second control means may be a software program to provide preprogrammed movement instructions to the medical device within the therapy head. Similarly the second control means may be a fixed or limited variable movement automatically added to the first control means movement instructions, to provide a wobble or other steady state variation to the robotic arm movement.

The therapy controller preferably has a three dimensional map (see section 3.0 below) of the treatment area prior to a therapeutic procedure actually beginning. The therapy controller can monitor the progress of the scan head during an actual procedure and compare it to the map of the tissue to be treated. Local progress of the treatment can be handled through a position tracking device used in conjunction with the therapy head of the present invention.

Procedurally the position control and tracking of the energy applicator is one way the system of the present invention can effectively destroy adipose tissue. Remarkable precision can be established in the adipose tissue so as to create lesions of destroyed tissue, or tissue necrosis. The precision is produced by utilizing a variety of position sensors and control devices for adjusting the position of the energy applicator.

The position of the energy applicator 600 within the therapy head 500 can be determined using the motor encoders linked to the micro motor assembly. By measuring the rotation of each of the motor axels using rotational encoders 530, the amount of movement of the actuators 508, 520, 516 connecting the motors 508, 510 to the energy applicator 600 can be determined. This is the first step in isolating the position of the energy applicator. Once the position of the energy applicator 600 is known within the housing 500 of the scan head 500, the position of the scan head 500 should be determined relative to the patient's anatomy. A series of optical sensors $555_1$, $555_2$ (FIG. 4A) can be used to precisely measure the physical distance the scan head travels over a patient's skin. These optical sensors can also be used to determine the rotational change (the amount the scan head rotates about its own center axis which is generally perpendicular to the skin of the patient), and the angular change (rotation relative to an axis that is not in the center of the scan head). In addition encoders in the articulating arm 200 can be used to determine the changes of position of the scan head 500 in three dimensions. Thus if the scan head 500 is moved over the side of a person's body, the three position sensing mechanisms will not be lost. The computer 400 or the therapy controller 250 can coordinate the data and keep track of position and dosage in a highly organized a precise manner. Optionally all data can be tracked on board, using an on-board processor 532. Division of processor duties can also help reduce load and speed up the response time between data reception and output of signals to the operator.

If for some reason the scan head loses track of the patient's skin, of the tracking system allows returning the scan head to the patient's skin and ensuring the proper orientation of the scan head so that the procedure can begin immediately with no guess work involved in trying to determine what tissue may have been treated and what tissue has not yet been treated. The repositioning involves placing the scan head on the reference position and aligning the scan head according to a flange (not shown) about the lower section of the housing.

The use of any of the three devices to determine and track position of the energy applicator allow for the display of the tissue map and a superimposed map dealing with the current treatment regime to be shown on a monitor, LCD or other device that can be properly interpreted by a user so he or she can determine where to move the scan head to continue with the procedure. The indicator to facilitate the treatment may be as simple as an audible tone of differing pitches (one tone for moving over an untreated area, and one tone for moving over an area already treated) to indicator lights, to a fully detailed video display. The display may be mounted external of the present system or used in conjunction with a computer, therapy control device, or on a smaller display mounted on, or in proximity to the scan head.

Methods of using the present invention are also disclosed. First there is a method for applying energy to a body region. The method comprises first providing a treatment plan to a therapy controller. Second manually scanning a scan head over a body surface in response to guidance generated by the therapy controller while energy is being delivered from the scan head. Third monitoring the position of and energy delivery from the scan head to produce position data and transferring the position data to the therapy controller and fourth generating an alert if the manual position and/or the energy delivery fall outside of the treatment plan. Preferably the method involves manually scanning the scan head over the body region prior to energy delivery to generate a virtual map of the region to be treated. The map is then loaded into the therapy controller. Other treatment parameters should be entered into the therapy controller to the extent possible. This helps to generate a treatment plan based on the virtual map and other treatment data.

System for Creating a 3D Volumetric Tissue Map

Figure 8:
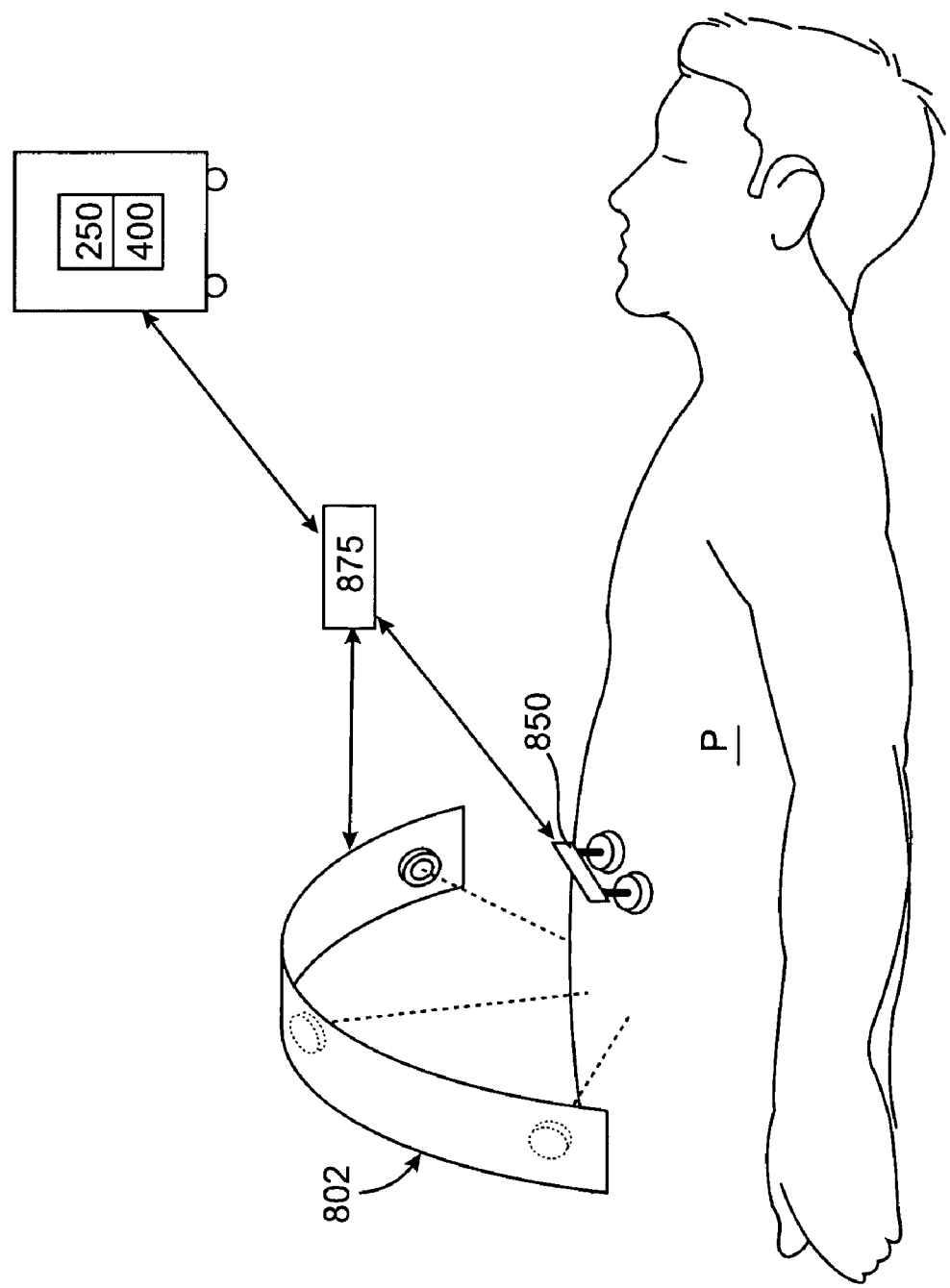
FIG. 8 illustrates a 3D volumetric imaging system.

There is also a system for producing a matched topographical and near surface subcutaneous tissue map (FIG. 8). The system has three components. First a three dimensional imaging apparatus 802 for producing surface images of a patient body. Second, a tissue imaging apparatus 850 for producing subcutaneous images of the patient body, and third, a correlative operation device 875 for matching a plurality of markers of said surface images and said subcutaneous images.

The three dimensional imaging apparatus may be a high resolution camera system or other optical camera capable of making detailed image maps of a patient skin surface. Resolution of skin features need not be a critical component of the camera system so long as it can accurately track the curvature and shape of the patient body region of interest. The volumetric imaging system may be a 3D ultrasound system or an interpolative 2D ultrasound imaging device. Alternatively the tissue imaging device may be an MRI or X-Ray device. Preferably both the visual imaging system and the tissue imaging system will produce electronic images which can be handled by a computer.

The correlative operation device may be a general purpose or specialized computer, or similarly capable intelligent logic device. The device may also be a software program. The correlative operation handles the matching of a plurality of markers between the surface and subcutaneous images in order to produce an accurate three dimensional tissue map. The markers used may be readily identifiable natural markers of the patient. However the markers are preferably a plurality of fiducials that can be detected by the two imaging devices. Once the images are captured, and stored electronically, the data of the two images can be correlated using the fiducials. It is not necessary for the two imaging systems to capture images in the same scale, as the correlative operation can also perform a scaling task to make sure one or both images are adjusted to a desired scale before correlation occurs.

Once the images are correlated, a new three dimensional map is produced. The new map has matched topographical and near surface subcutaneous features. The fiducials used by the system may have a variety of parameters that can assist in correlating the image maps. For instance, the fiducial may include an indicator of up or down so the imaging system can determine the orientation of the fiducial after the image is captured. Using a plurality of fiducials with orientation data, it is possible to precisely determine the matching over lay position of the second image produced by the system. The fiducial is preferably detectable by both image systems (surface and subcutaneous), however this is not required. A user may place a plurality of fiducials on a patient body detectable by one imaging system and not the other, so long as the user replaces the fiducials with others that the second system can detect, the correlative operation can still be used effectively.

Methods of Use

The methods described herein are non-invasive. Unlike traditional liposuction procedures utilizing a cannula with a vacuum, there is no penetration of a patient's skin. The destruction of fat cells or adipose tissue occurs via the build up of heat or the mechanical disruption caused by cavitation, both effects produced by directed irradiation and preferably by high intensity focused ultrasound (HIFU). Thus in a non-invasive procedure for reduction of adipose tissue, there is no way to directly visualize how much tissue has been affected. In liposuction, a treating physician is able to visualize either the amount of fat removed or destroyed, but in a non-invasive procedure, this direct observation is not possible. The user of the present invention will have to rely on a diagnostic ultrasound device or other sensor to help determine the volume of treated tissue.

Figure 9A:
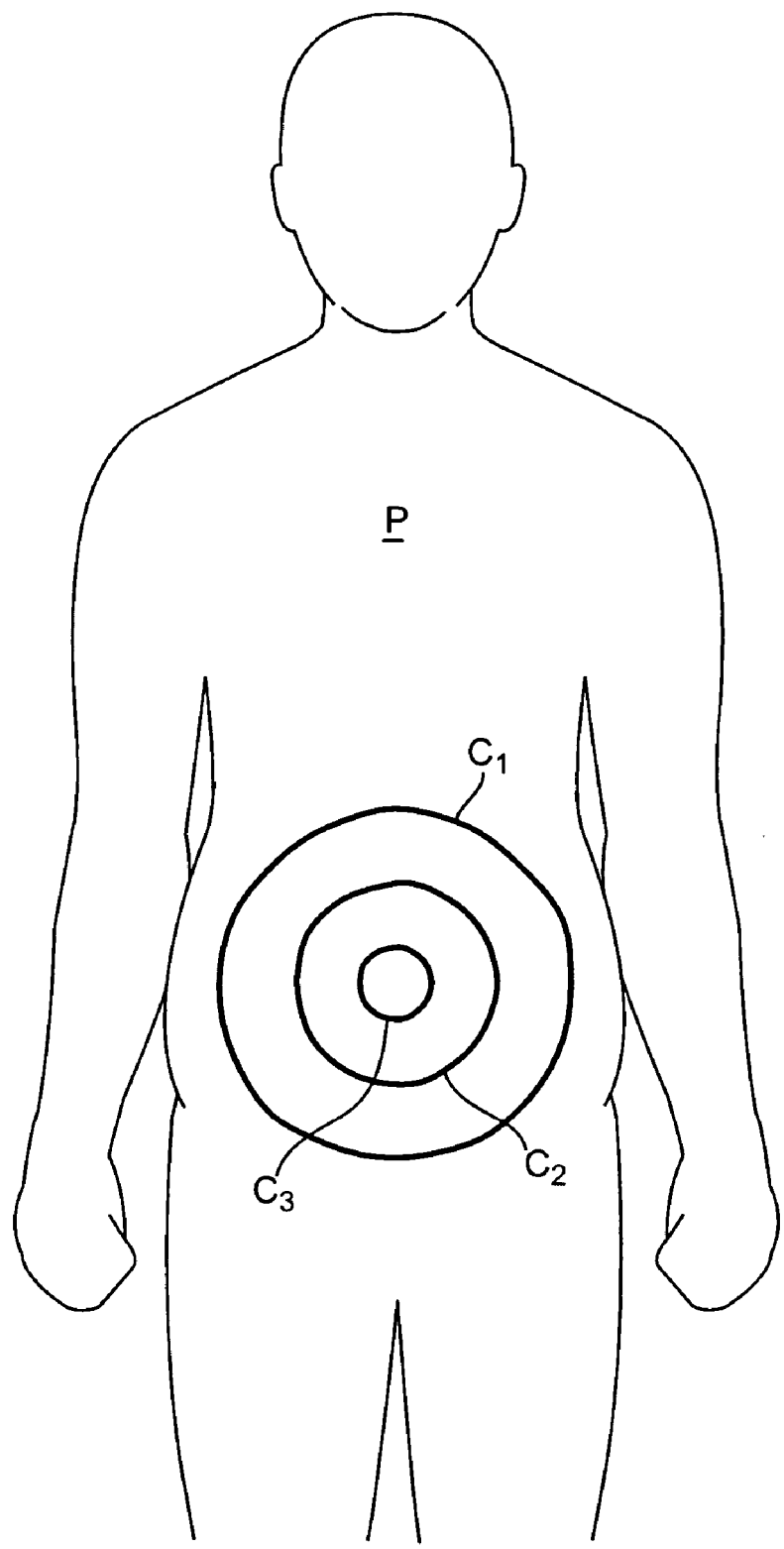
FIGS. 9A-C illustrate a method of marking a patient body.

A common aspect of the methods described herein is an evaluation of the regions of adipose tissue to be treated. Current techniques using a "pinch" test can provide a reasonable starting place for the use of both the systems and methods described herein. The pinch test is used by plastic surgeons to evaluate regions of adipose tissue. A patient P may have local adipose tissue he or she wishes to have removed. A physician can evaluate the adipose tissue by drawing a series of contour lines $C_1, C_2, C_3 \ldots C_x$ on the patient (FIG. 9A).

Method of Applying Ultrasound Energy to a Body Region

In one embodiment, the method of the present invention provides a method for applying energy to a body region. The method has four steps. The first step is providing a treatment plan to a treatment controller. The second step is scanning a scan head over a body surface in response to guidance generated by the treatment controller while energy is being delivered from the scan head. The third step is monitoring the position, and energy delivery of the scan head to produce position data and transferring the position data to the treatment controller. The fourth step is generating an alert if the position and/or the energy delivery fall outside of the treatment plan.

In step one, a treatment plan is provided to a treatment controller. Here the user identifies the need of the patient to be treated and selects a treatment plan according to the patient need. In the preferred application of destroying adipose tissue, the user will select from a possible list of options on how much adipose tissue is to be destroyed, the pace of the tissue destruction, depth, energy flux and other parameters needed. The user will probably not be familiar with the technical elements that contribute to each treatment plan, but will select based on the desired result. Such as selecting a plan to destroy adipose tissue along a 12 cm line of 8 cm wide and 2 cm deep. The program variables a user can understand are more in line with the result than the way the machine operates to achieve the result. Once the treatment plan is selected, the user enters the desired treatment plan into the treatment controller. The treatment controller determines an operational protocol that will produce the desired treatment plan.

The second step involves the scanning of the patient with the scan head. The scan head (or therapy head) is active such that ultrasound energy is transmitted into the patient to destroy adipose tissue. The scan head is moved in accordance with the protocol from the treatment controller. The movement may be achieved through manual means or automated means. In a manual mode the treatment controller provides cues for the user to follow. The user moves the scan head over the patient in response to the cues. In an automated means, the treatment controller directly controls a device or apparatus, such as a robotic arm, to direct the movement of the scan head.

The third step is to monitor the position and the energy delivered by the scan head. The position and delivery information is communicated to the treatment controller in the form of a data feed that is compared to the protocol the therapy controller is using (either through a user, or a robotic device). The therapy controller is continuously monitoring the incoming data against the protocol to ensure the safety of the patient during a procedure.

The fourth step is an alert. If either the position or energy delivery are outside the acceptable tolerance of the protocol, the therapy controller issues an alert. The alert may be strictly for the user to monitor, or it could be a built in cut off switch to immediately shut down any energy emitter in the scan head.

Step one is selected at the outset of the procedure, however steps two, three and four are performed continuously to ensure the proper therapy regimen is applied to the patient.

Method for Performing Lipoplasty Therapy

In a second embodiment, there is a method for performing a lipoplasty procedure. The method having the steps of first, determining the suitability of a person for therapeutic ultrasound treatment. Second, marking the areas to be treated on the person. Third, positioning the patient for a therapeutic ultrasound procedure. Fourth, scanning the marked areas into a computer, fifth, setting the therapeutic ultrasound procedure using a procedure planning software package. Sixth, activating the therapeutic ultrasound procedure using a computer system controlled through the procedure planning software. Seventh is recording the progress of the therapy procedure using the procedure planning software, and finally, providing the person with any additional post operative assistance as may be dictated.

The methods of the present invention are ideally suited to provide for the maximum amount of safe, long term correction to a body sculpting procedure with the option for additional therapy treatment and drug regimen usage, while at the same time maintaining a virtual map of the patient to ensure the treatment is effective and safe over the long term.

Taken together, the methods disclosed combine into yet another aspect of a method to perform a lipoplasty procedure comprising the steps of:

(a) determining the suitability of a person for therapeutic ultrasound treatment;
(b) marking areas to be treated on a the person;
(c) positioning the patient for a therapeutic ultrasound procedure;
(d) scanning the marked areas into a computer;
(e) setting the therapeutic ultrasound procedure using a procedure planning software package;
(f) activating the therapeutic ultrasound procedure using a computer system controlled through the procedure planning software;
(g) recording the progress of the therapy procedure using the procedure planning software; and
(h) providing the person with any additional post operative assistance as may be dictated.

The following example illustrates the method described.

Example I

Step 1: The patient comes in for an initial consultation, just as in traditional lipoplasty. If the patient decides to continue on to the procedure, dietary supplements, drugs, topical creams, etc. that may be formulated specifically to provide some benefit during or after the procedure may be provided. Examples include Bromelain and Quercetin taken prior to the procedure and Arnica Montana taken post-procedure to promote healing and reduce swelling.

Step 2: On the day of the procedure, the physician marks the patient in a manner similar to what would be done for traditional lipoplasty patients. The ink in the marking pen may contain an additional agent (e.g. an ultraviolet ink) to enhance detectability of the ink on the skin by a sensor. This may be particularly useful for dark skin colors.

Step 3: The patient is positioned for the procedure. The patient should be in the same position as he or she will be during treatment. In most case the procedure is done with the patient laying on a bed, so this pre-op step is done with the patient laying prone. The patient's fat thickness may be mapped out over the areas to be treated, for example with ultrasound. A diagnostic ultrasound system may be combined with an image analysis system that detects the strong reflection from the boundary between fat and underlying muscle, and records this thickness along with position information. The position information comes from a position sensing device attached to the ultrasound transducer. Since depth-only information is needed, the diagnostic ultrasound unit may be replaced with a simpler pulse-echo A-line system. Reference marks may be drawn on the patient's body, or marked in another way such as with stickers, to provide reference locations for the position sensing system. This map of fat thickness, or a subset thereof may be stored for reference on a subsequent patient visit, e.g. to visually demonstrate actual effects achieved.

Step 4: The pre-procedure body marks are scanned into a computer, also using a position sensing system as described above. This may be done by tracing drawn marks with a stylus coupled to the positioning system, or through optical detection of markings in coordination with the positioning system. Ideally, this map of markings scanned into the computer may be referenced to the fat thickness map that may have been acquired as described above. The positioning system typically records three to six degrees of freedom (i.e. x, y, z, pitch, yaw, roll) in all cases.

Step 5: The practitioner may now interact with procedure planning software provided on a computer with access to the marking and thickness data acquired as per above. We expect that we will be able to control aesthetic effect of our procedure locally, e.g. by varying depth, time, or density of treatment to affect more or less tissue. The point of the procedure planning software is to connect these system variables to the desired overall aesthetic effect to be achieved. For example, the practitioner may decide that an area of fat should be reduced by 2 cm in a central area, tapering off to 1 cm in an outlying region, "feathering" off to zero effect outside that region. The practitioner does this by identifying the desired effect on a visual representation of drawn contours, and optionally fat thickness. Drawn contours and marks may be edited or modified in the treatment planning software. The user may, for example, by identifying the 2 cm region by clicking inside the corresponding pre-procedure mark with a mouse, or pointing at it on a touch-sensitive surface, and either typing or selecting from a menu that this region corresponds to 2 cm thickness. If the contours need to be modified, they may be altered through the software through means that are typically found in drawing software like Adobe Illustrator. For example, if a Bezier representation of drawn contours is maintained by the software, Bezier "handles", "control points" or "knots" may be provided for user interaction and modification as is typical in drawing software. The 1 cm area is identified in a similar way. Transition regions may be identified, for example by simply choosing a fixed distance on one or both sides of the 2 cm contour for a gradual transition to 1 cm, and the same for the transition from 1 cm to zero. Transition distances may be variable, and may in fact be drawn into the computer with a pointing device, or may be represented by pre-surgical markings that are scanning into a computer and identified as transition regions to the planning software. The user may also inform the therapy controller what effect is desired in a transition region, e.g. a linear falloff or some other shape of curve, and what combination of system variables (e.g. depth, power, time, density) should be used to achieve the effect. Depths, transition areas, variables affected, etc. may be shown visually in different colors or with different markings for ease of identification. When the editing and identification process is complete, the computer calculates a treatment plan relating all relevant system variables to the desired aesthetic effect.

Step 6: During the course of actual therapy, the therapy head containing the high-intensity ultrasound transducer(s) is connected to a positioning system as described above that allows a system computer to relate the current position of the therapy head to the computer representation of the treatment plan. The computer then controls therapy variables to achieve the desired aesthetic effect. In the example above, as the therapy head is moved through the 2 cm region, appropriate power, pulse duration, etc. is applied to the therapy head to achieve 2 cm of affected tissue. As the head is moved through a transition region to the 1 cm area, power and duration may be reduced in order to affect a varying thickness of tissue until 1 cm effect is achieved. Similarly, this "feathering" effect is achieved as the head is moved outside of the 1 cm area, and the transducers are not allowed to fire if the head is outside the treatment area. The overall treatment plan and record may be stored for future reference.

Step 7: After therapy, the patient may be asked to wear a compression garment over treated areas as is common with traditional lipoplasty procedures, and may be given other drugs or nutritional supplements to promote healing or reduce discomfort.

Method of Destroying Adipose Tissue Using HIFU

In a third embodiment there is a method of destroying adipose tissue in a patient using therapeutic ultrasound. The method having the steps of: first determining one or more locations of adipose tissue on the patient. The second step is positioning the patient such that the adipose tissue settles into a relatively even distribution (preferably facing upward), and third, irradiating the locations of adipose tissue of the patient with a therapeutic ultrasound transducer.

In this method, the location and size of the adipose tissue area to be treated must first be determined. This may be done through traditional means like the "pinch" or "clamp" test routinely used by plastic surgeons, or it may be determined by using a medical scanner such as a diagnostic ultrasound system or the three dimensional topographical map device previously described. The locations of adipose tissue must be located and properly identified as to depth and size. So while a physician may rely with great comfort on his or her skill using the pinch test, the boundaries and depths of the adipose tissue must be evaluated as accurately as possible. Thus an imaging scanner of some kind is required. Once the tissue volumes and depths are determined, the skin may be marked with a surgical pen or other device so the user will be able to clearly identify the zones to be treated.

Next the patient is oriented in a manner that will promote the success of the irradiation step. Here the patient is oriented on a bed or chair in a manner so the adipose tissue to be treated is facing up as much as possible. This allows the adipose tissue to settle into a fairly even distribution about a center, so tissue depth is preferably symmetrical for treatment.

Finally the regions of adipose tissue are treated. The volumes of adipose tissue are treated with a therapeutic ultrasound transducer. The treatment can be uniformly applied if the layer of tissue has settled evenly and uniformly in step two.

Method of Creating a Three Dimensional Body Map

A method of creating a three dimensional body map is also described. The method of creating a 3D body map with the locations of adipose tissue volumes has the steps of: First, generating a 3D image of the body using a 3D imaging system. Second, entering the 3D image of the body into a computer readable format. Third, creating a 3D body map of the body with a 3D mapping software application, and fourth, scanning the body with a diagnostic ultrasound device in electronic communication with the 3D mapping software application such that the regions of adipose tissue detected by the diagnostic ultrasound device are properly placed in the 3D body map.

The details of this first method are as follows. A 3D imaging system comprises a plurality of cameras which take a snap shot of the patient. The snap shot involves all the cameras of the 3D imaging system taking a picture simultaneously. Thus a visual image can be captured of the entire body from all sides. In order for this to be done, the patient likely must undress and stand nude or semi-nude at the focal point of the imaging system. The imaging system is similar to those used to make auto commercials that show an automobile from all angles simultaneously. The images from the 3D camera system are overlapped and coordinated properly so a single comprehensive image of a person's body is generated. The imaging system used is highly accurate and can be converted into machine readable form.

The cameras in the 3D imaging system may take normal film images or digital images. However regardless of the image type taken, the images must be properly over laid so a single image of the body results. The image is then converted to a 3D topographical map of the human body and stored in the computer. The procedure relies on the accuracy of the 3D image capturing system to accurately reconstruct the image of the body. Then the software must properly convert the image into a topographical map. Once the topographical map of the human body is generated, the data can be stored for later retrieval. This first image is the pre-op 3D map of the patient.

Once the pre-op map has been made, the patient undergoes a diagnostic ultrasound scan. The scan may be as simple as an a-line or b-mode scan to determine fat density and depth in a given area. However the preferred mode is a high resolution imaging system so that details of the adipose layers may be visualized and recorded. The diagnostic imaging system is in electronic communication with the computer, software and pre-op map. By using a position location sensor, or a precision location controller, the position and direction of the diagnostic scan relative to the body is recorded and superimposed on the pre-op map. This allows a physician to generate a volumetric map of a person's fat deposits. The super imposed imaging allows both patient and physician to see what areas are available for treatment (either invasive or non-invasive) as well as play with the models by sampling a certain amount of fat to be removed and seeing what the patient would look like. This involves the generation of an abstract model using the pre-op model as the base line, and any projected changes to the pre-op model to visualize the final out come.

Method of Using a 3D Body Map

In another embodiment there is a method of body sculpting utilizing a 3D body map. The method having the steps of first analyzing the 3D body map for volumes of adipose tissue to be destroyed. The second step is determining the amount of adipose tissue that may be safely destroyed using a body sculpting procedure. The third step is subtracting the volume of adipose tissue destroyed to produce a second 3D body map, wherein a physician and a patient may compare the first 3D body map and any number of second 3D body maps to select the desired amount of body sculpting procedure to be performed.

In this method a first body map is created using the imaging systems disclosed herein. The first body map represents the starting point for a patient before any therapy procedures are initiated. The therapy controller can be used to create a second map showing the body contoured after a volume of adipose tissue is destroyed. By using the therapy controller in this way, it is possible for a patient to see a potential end result of the therapy treatment in numerous types of treatment. Thus the patient and physician can get an estimate of what the patient will look like based on a 3D body map of the person after one or more treatments. This information can be used by the physician and patient to guide the procedures and determine a safe number of treatments for the desired goal, or determine the maximum amount of adipose tissue that can be destroyed for a certain number of treatments.

Other Methods of Destroying Adipose Tissue

In an alternative embodiment for destroying adipose tissue, there is a method for destroying adipose tissue having the steps of first determining a volume and area of tissue to be treated, and second treating that volume using a pulse wave HIFU transducer swept over the area o tissue in a continuous motion.

In operation, the step of determining the presence and location of adipose tissue may be very similar to the method previously illustrated and using a 3D imaging system with a computer to create a pre-op model. However current procedures in liposuction offer an aspect of quickly determining regions of adipose tissue by using a marker on the skin of the patient. In this manner a physician, using his or her own experience and practical training, is able to identify the "problem" areas a patient desires to operate on. The physician uses a marker to out line the area of skin, representing the region of adipose tissue. Once this is performed, the patient may go through the process of creating a 3D pre-op model as above, however the cameras have the advantage now of being able to detect and incorporate the marked regions on the skin into the 3D topographical map. The ink used in the marker may contain a special dye or pigment that allows the cameras to visualize it under special conditions. E.g. the use of a fluorescent dye visible under a special light.

Positioning the patient occurs similar to the procedure previously described. Then the patient is treated with a high intensity focused ultrasound (HIFU) device to destroy selected regions of adipose tissue. The HIFU device is particularly designed to incorporate the precision location sensor, or positioning mechanism used in the diagnostic ultrasound step described above. In this manner the direction and location of the ultrasound treatment is known and can be super imposed on the pre-op map of the patient. Additional detail can be recorded if the high intensity focused ultrasound electronics are also tied to the imaging system so that each pulse or transmission of the HIFU transducer can be recorded and super imposed on the pre-op map in real time. In this manner the irradiation step of the procedure can be performed safely and precisely since the computer can record every single position of treatment.

By using a feedback communication loop between the computer recording the data of HIFU treatments, and the HIFU transducer, an enhanced safety feature is realized in that the computer can prevent the HIFU transducer from firing into a region that has already been treated, or by insuring there is some minimum level of spacing between lesions. This spacing may be the three-dimensional geometry of the lesions, or a more complicated spacing in time. Where a patient may come in for multiple treatments, the system remembers the location of previous HIFU lesions and prevents the irradiation of the same volume until an adequate space of time has elapsed. A combination of 3D geometry and time sequence of the lesions can also be controlled by the computer system, as well as incorporating additional parameters for the strength, size and duration of the HIFU treatment.

When the irradiation procedure is completed, the patient may be re-scanned using the diagnostic imaging device to determine the extend of the procedures success as planned. From the post op evaluation, the physician may plan and schedule additional treatments, or modify the schedule of already planned additional treatments to suit the needs of the patient in a safe and efficacious manner.

Depending on the extent of the treatment performed on the patient, the patient may be discharged with additional medications, or with compression clothing to assist in the healing or sculpting of the body.

Example II

Figure 9B:
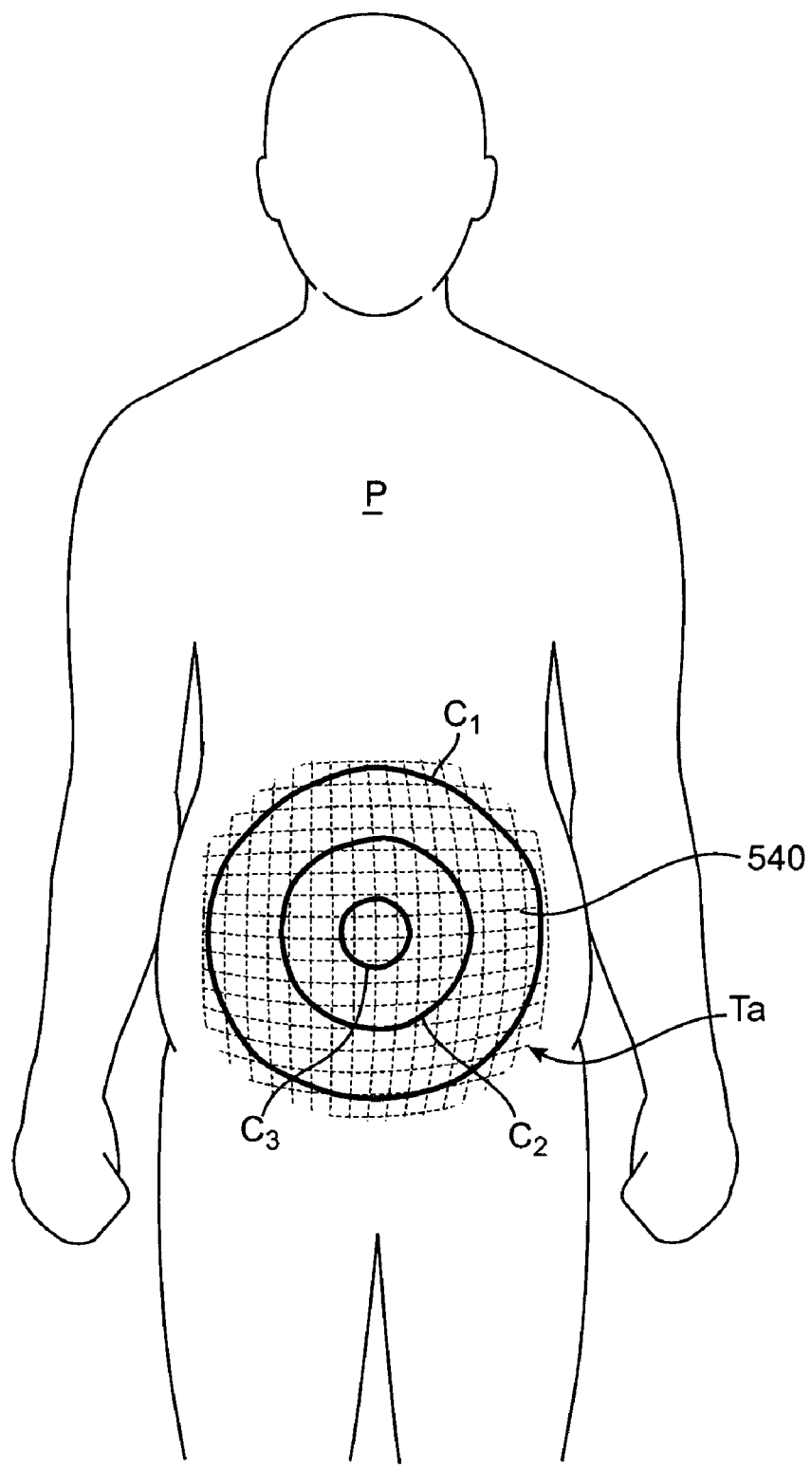
Figure 9C:
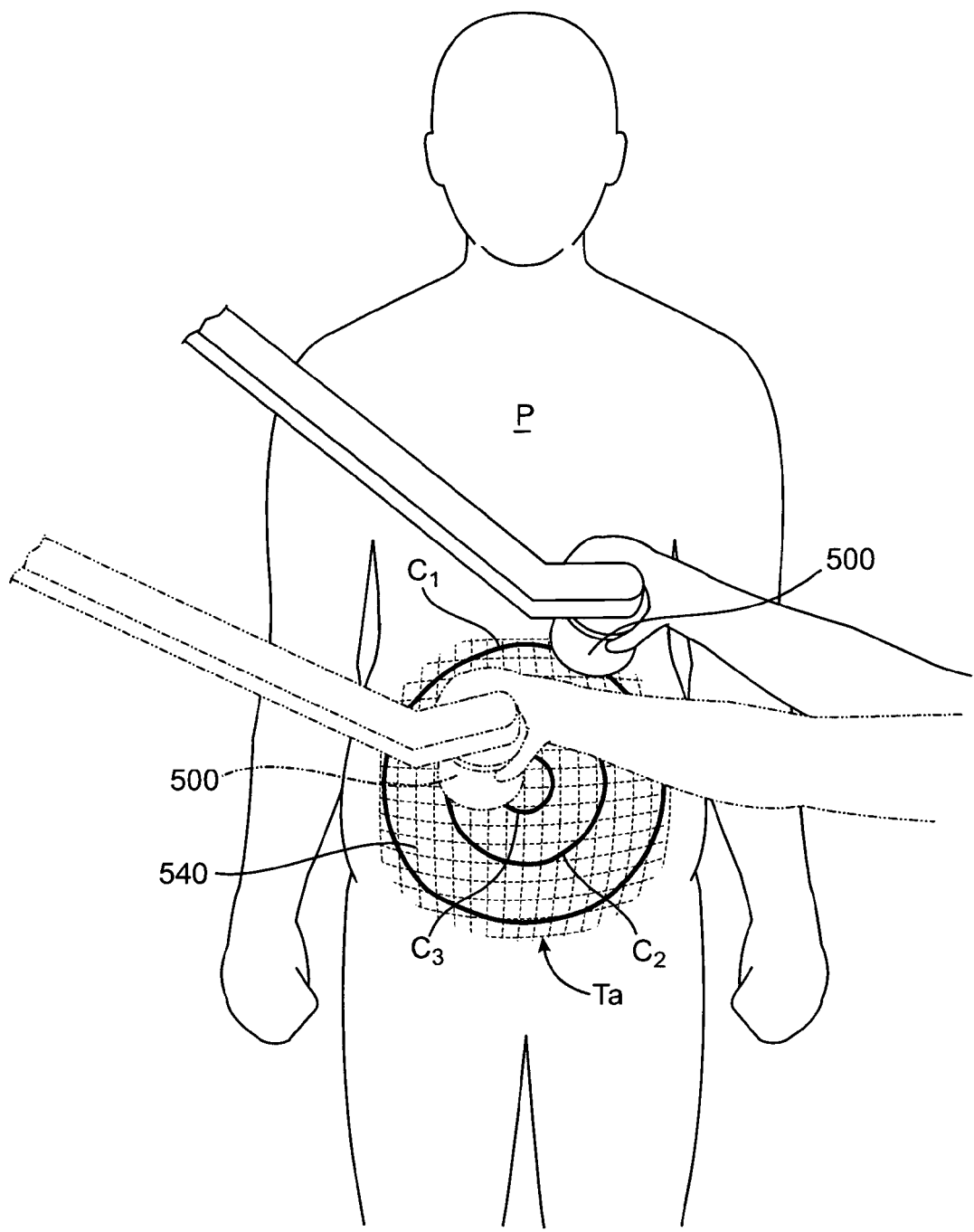

This method of destroying adipose tissue involves the use of the aforementioned therapy head with a simultaneous scanning and pulse wave transducer regimen. In this method the patient is prepared in the same manner as previously described. A set of contour lines are laid down to identify the area corresponding to the tissue volume to be treated (FIG. 9A). Lines or grid squares may be over laid on the contour lines (FIG. 9B). The therapy head is used to scan the tissue area to verify there is sufficient depth of adipose tissue (FIG. 9C). Once that is done, therapy may begin.

Therapy is performed by moving the scan head over the treatment block at a speed of 3 mm/sec. to 50 mm/sec., using a therapy transducer with a pulse wave mode. The robotic arm may move the transducer, or the user can move the therapy head with the instrument keeping track of the distances moved during each sweep.

The micro-positioning system can also be used with in the therapy head to sweep across the line of movement of the therapy head. This allows a larger area to be treated and subsequently a greater volume. This allows for the volume of necrosed tissue to be enhanced, lowering the time required to treat the volume, and bring the non-invasive procedure closer in time to an invasive procedure.

In another method for destroying adipose tissue, three general steps are performed. The first step is to determine a volume and area of tissue to be treated. Second to treat the volume and area of tissue, and finally to determine the efficacy of the treatments for the volumes and areas.

The first step involves determining the volume and area of the tissue to be treated. Currently plastic surgeons rely on their years of experience to determine the amount of adipose tissue a patient may have. Tactile examination allows physicians to create contour lines around areas of adipose tissue to be removed with liposuction. This same method may be used as a starting point for the physician to create contour lines. The depth of the adipose tissue under the contour lines needs to be verified using an ultrasound scan.

Once the contour lines are established, the patient must be oriented so the contour lines that are to be treated are positioned in a manner to make the tissue accessible to the therapy head. The therapy head desirably has a wide range of motion, but orientation of the patient is important since many orientations the therapy head can achieve are neither comfortable nor practical for the user of the instrument, or the patient to be treated. In general, the orientation should be with the surface area of the adipose tissue to be facing up and generally flat. This allows for the adipose tissue to "settle" into a stable volume without being overly concentrated on one side, as opposed to when the patient may be resting to present the volume and surface to be treated in a manner where the tissue settles irregularly. The regularity in the tissue depth and volume will also assist the user to deliver a more uniform and effective treatment.

After the patient has been oriented in a manner conducive to the user, therapy head and patient comfort, the therapy head is used through out the contour line area in a diagnostic scan mode. This scanning of the patient to verify adipose tissue depth is needed to provide accurate information to the system and user so that the therapy head does not destroy tissue that it should not. Simply put, it is necessary to verify there is sufficient depth of adipose tissue within the contour line area before treatment begins. If insufficient adipose tissue depth is found, the contour line must be redrawn so that the safety standards are met.

Assuming the adipose tissue depth and volume is sufficient to initiate a therapy procedure, the user can commence the marking of a treatment zone grid on the patient body. The treatment zone grid desirably is at least as large as the area surrounded by the contour lines, and probably extends beyond the contour lines. The treatment zone grid may be marked on the patient with a surgical marker, a roller device or spray on ink with a template or stencil. Other manners of producing the treatment zone grid are possible.

After the tissue volume has been confirmed and the treatment zone grid has been placed, the user may enter the patient data and the desired treatment parameters into the therapy device using the host interface. Various parameters can be entered into the device and the user may accommodate whatever information is needed or desired. Once the machine has been properly programmed, the main step of determining the volume and area of tissue to be treated is completed and the user can proceed to the second main step of the actual treating of the volume and area of tissue.

First the user places the therapy head on to the patient body and in alignment with the treatment zone grid. If the therapy head has fiducial markings on it that can be aligned with the treatment zone grid, the fiducials should be so aligned. This allows the therapy head to be accurately positioned for treatment. If there is a readily identifiable pattern, such as a notable starting place like a corner or other position in the treatment zone grid, then the user can begin there. In addition the therapy controller or host interface may have a tracking system for determining what areas have been treated so the user does not need to keep track of that information.

Next, the user identifies a treatment zone to be scanned with a therapy head. This will be the first scanned area and there will be as many scan areas as number of times the foot print of the scan head can be fit into the contour line areas. With the therapy head in position, the diagnostic scanner may be run again to verify sufficient tissue depth. The diagnostic scan may be run interleaved with the therapy scanner, or simply at the outset of the therapy block.

The therapy block is the area under the therapy head to be treated. The HIFU transducer is engaged according to the parameters from the therapy controller. The transducer either mechanically scans the block area, moving via a micro-positioning system, or the focal region is moved electronically using a an electronically steered HIFU transducer (such as a phased array). The depth of the lesion, density and size can be affected by the scan speed of the transducer (how fast the focal point is either electronically or mechanically moved through the tissue). Altering the intensity, PRF or overlap of the treatment lines can also affect the lesion size and shape. By adjusting one or more of these parameters it is possible to produce lesions both big and small, deep or shallow and permit a user a level of control over the level of necrosis. Thus the user can reduce the amount of necrosis and produce a feathering effect, so that as the therapy head approaches the border of the adipose tissue, the amount of tissue necrosis is reduced. This permits the desirable tissue treatment without risking damaging non-adipose tissue. It also permits the user to enlarge the zones of necrosis in deep adipose tissue areas to generate larger regions of necrosis to produce the desired results.

Lesion feathering and uniform treatment values—between the contour lines the treatment density is varied from the uniform treatment value with the feathering treatment function.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

What is claimed is:

1. A system for the application of energy into a body region, the system comprising:
    a base unit containing a therapy controller;
    a mechanical arm having a proximal end and a distal end, the proximal end being mounted to said base, the mechanical arm having a plurality of degrees of freedom; and
    a scan head movably mounted to the distal end of said mechanical arm, the scan head comprising:
        an upper chamber having two motor drive units operating in coordination to move two traveler rods;
        at least one encoder coupled to each motor drive unit for determining the position of the traveler rods; and
        a lower chamber having (1) an interior filled with a coupling fluid and sealed from the upper chamber by a wall having at least one aperture for receiving said traveler rods and (2) an energy aperture at a lower end thereof for broadcasting energy from the scan head; and
        a slotted actuator connected to each traveler rod to be rotated by the motor drive unit;
        an energy applicator within the lower chamber and removably attached to said slotted actuators wherein said motor drive units operate to move said energy applicator over the energy aperture within the confines of the lower chamber; and
        at least one electronic unit connecting the therapy controller, said motor drive units, said encoder(s) and said energy applicator such that the therapy controller is in electronic communication with said motor drive units, said energy applicator and said encoder(s) such that the therapy controller can control the position of the energy applicator within said lower chamber based on data received from said encoder(s).

2. A system as in claim 1, wherein the energy applicator comprises at least one vibrational transducer.

3. A system as in claim 1, wherein the scan head further comprises a controlled energy applicator mounting system comprising the motor drive units in electronic communication with the therapy controller, whereby the therapy controller can adjust the position of the energy applicator within the scan head.

4. A system as in claim 1, further comprising a navigation display in electronic communication with the therapy controller, whereby the therapy controller can display guidance information for a user.

5. A system as in claim 4, wherein the navigation display comprises a video screen or a liquid crystal display (LCD), and communication means for communicating with said therapy controller.

6. A system as in claim 4, wherein the navigation display is mounted on the mechanical arm adjacent to the scan head.

* * * * *